US010344333B2

(12) United States Patent
Testa et al.

(10) Patent No.: US 10,344,333 B2
(45) Date of Patent: Jul. 9, 2019

(54) METHODS FOR DIAGNOSING A PREDISPOSITION TO DEVELOP CANCER

(75) Inventors: Joseph R. Testa, Philadelphia, PA (US); Michele Carbone, Honolulu, HI (US); Mitchell Cheung, Philadelphia, PA (US); Jianming Pei, Philadelphia, PA (US)

(73) Assignees: Institute For Cancer Research, Philadelphia, PA (US); University of Hawaii, Honolulu, HI (US)

( * ) Notice: Subject to any disclaimer, the term of this patent is extended or adjusted under 35 U.S.C. 154(b) by 1048 days.

(21) Appl. No.: 14/000,382

(22) PCT Filed: Feb. 17, 2012

(86) PCT No.: PCT/US2012/025578
§ 371 (c)(1),
(2), (4) Date: Sep. 11, 2013

(87) PCT Pub. No.: WO2012/112846
PCT Pub. Date: Aug. 23, 2012

(65) Prior Publication Data
US 2014/0011699 A1    Jan. 9, 2014

Related U.S. Application Data

(60) Provisional application No. 61/444,438, filed on Feb. 18, 2011, provisional application No. 61/524,959, filed on Aug. 18, 2011.

(51) Int. Cl.
C12Q 1/68        (2018.01)
C12P 19/34       (2006.01)
C12Q 1/6886      (2018.01)

(52) U.S. Cl.
CPC ..... *C12Q 1/6886* (2013.01); *C12Q 2600/156* (2013.01)

(58) Field of Classification Search
CPC ............ C12C 1/6886; C12C 2600/156; C12Q 1/6886; C12Q 2600/156
See application file for complete search history.

(56) References Cited

U.S. PATENT DOCUMENTS

| | | |
|---|---|---|
| 2003/0148364 A1 | 8/2003 | Swift et al. |
| 2009/0149511 A1 | 6/2009 | Burk |
| 2012/0077682 A1 | 3/2012 | Bowcock et al. |
| 2014/0010802 A1* | 1/2014 | Testa ............... C12Q 1/6886 424/94.63 |

OTHER PUBLICATIONS

SNP linked to Gene (geneID:8314) via Contig Annotation, SNPs in the coding region of the BAP1 gene, pp. 1-6 printed from https://www.ncbi.nlm.nih.gov, printed on Dec. 9, 2016.*

Baker K.E. et al. Current Opinion in Cell Biology, 2004, 18:293-299.*
Altomare, et al., "Activated Tnf-a/NF-kB signaling via down-regulation of Fas-associated factor 1 in asbestos-induced mesotheliomas from Arf knockout mice", PNAS, Mar. 3, 2009, vol. 106, No. 9, pp. 3420-3425.
Genbank Accession No. CV814206.
Genbank Accession No. NM_004656.3.
Genbank Accession No. ss101353157.
Harbour, et al., "Frequent Mutation of BAP1 in Metastasizing Uveal Melanomas", Science, Dec. 3, 2010, 330 (6009):1410-1413.
International Search Report issued in PCT/US12/25578 dated Aug. 23, 2012.
Jensen, et al., "BAP1: a novel ubiquitin hydrolase which binds to the BRCA1 Ring finger and enhances BRCA1-mediated cell growth suppression", Oncogene, Mar. 5, 1998, 16(9):1097-112.
Li, et al., "Wild-type BRCA1, but not mutated BRCA1, regulates the expression of the nuclear form of beta-catenin", Mol. Cancer Res., Mar. 9, 2010, vol. 8, No. 3, pp. 407-420.
Testa, et al., "Germline-BAP1 mutations predispose to malignant mesothelioma", Nat. Genet., Aug. 2011; vol. 43, No. 10, pp. 1022-1025.
Timakhov, et al., "Recurrent Chromosomal Rearrangements Implicate Oncogenes Contribuing to T-Cell Lymphomagenesis in Lck-MyrAkt2 Transgenic Mice", Genes Chromoosomes Cancer, Sep. 2009, 48(9):786-794.
Uematsu, et al., "Targeting the Wnt signaling pathway with dishevelled and cisplatin synergistically suppresses mesothelioma cell growth", Anticancer Res., Nov./Dec. 2007, vol. 27, No. 6B, pp. 4239-4242.
Ventii, et al., "BRCA1-associated protein-1 is a tumor suppressor that requires deubiquitinating activity and nuclear localization", Cancer Res., Sep. 1, 2008, vol. 68, No. 17, pp. 6953-6962.
Wood, et al., "The Genomic Landscapes of Human Breast and Colorectal Cancers", Science, Nov. 16, 2007, vol. 318, pp. 1108-1113.
Lu, Y. et al., "Issues Related to Targeted Delivery of Proteins and Peptides", The AAPS Journal, 2006 8(3) Article 55, E466-E478.
Genbank Accession No. NT_022517.
Thomas, J.A. et al., "Toxicological Assessment of Zeolites", Journal of the American College of Toxicology, 1992, 11(3):259-273.
Holly, E.A. et al., "Intraocular Melanoma Linked to Occupations and Chemical Exposures", Epidemiology, 1996, 7(1):55-61.
Ismail et al., "Germline Mutations in BAP1 Impair Its Function in DNA Double-Strand Break Repair", Cancer Res., 2014, 74(16):4282-4294.

(Continued)

*Primary Examiner* — Stephen T Kapushoc
(74) *Attorney, Agent, or Firm* — Stradley Ronon Stevens & Young, LLP

(57) ABSTRACT

Systems, methods, and computer readable media for diagnosing or characterizing a genetic predisposition to develop cancer are provided. Nucleic acids comprising a germline nucleic acid sequence encoding the BRCA1 associated protein 1 are sequenced or probed to determine if the nucleic acid sequence includes alterations that predispose a subject to develop cancer.

8 Claims, 13 Drawing Sheets
Specification includes a Sequence Listing.

(56) References Cited

OTHER PUBLICATIONS

Carbone et al., "BAP1 and Cancer", Nature Reviews Cancer, 2013, 13:153-159.

Napolitano et al., "Minimal asbestos exposure in germline BAP1 heterozygous mice is associated with deregulated inflammatory response and increased risk of mesothelioma", Oncogene, advance online publication, 2015, 1-7.

Carbone et al., "Combined Genetic and Genealogic Studies Uncover a Large BAP1 Cancer Syndrome Kindred Tracing Sack Nine Generations to a Common Ancestor from the 1700s", Plos Genetics, advance online publication, 2015, 1-14.

Yu et al., "Tumor Suppressor and Deubiquitinase BAP1 Promotes DNA Double-Strand Break Repair", Proc Natl Acac Sci USA, 2014, 111:285-290.

GeneCards output for BAP1, from www.genecards.org, printed on Aug. 26, 2015, pp. 1-22.

Non-Final Official Action dated Feb. 10, 2017 received in related U.S. Appl. No. 13/969,986.

\* cited by examiner

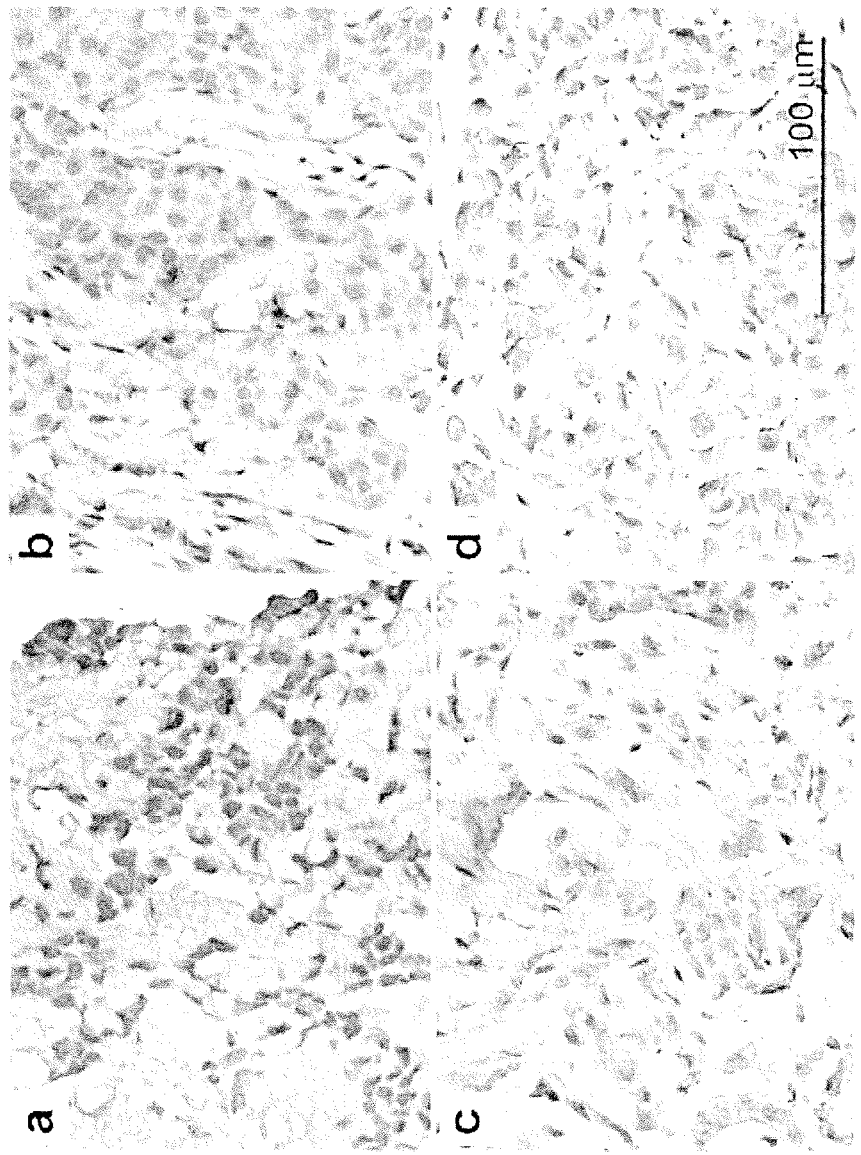

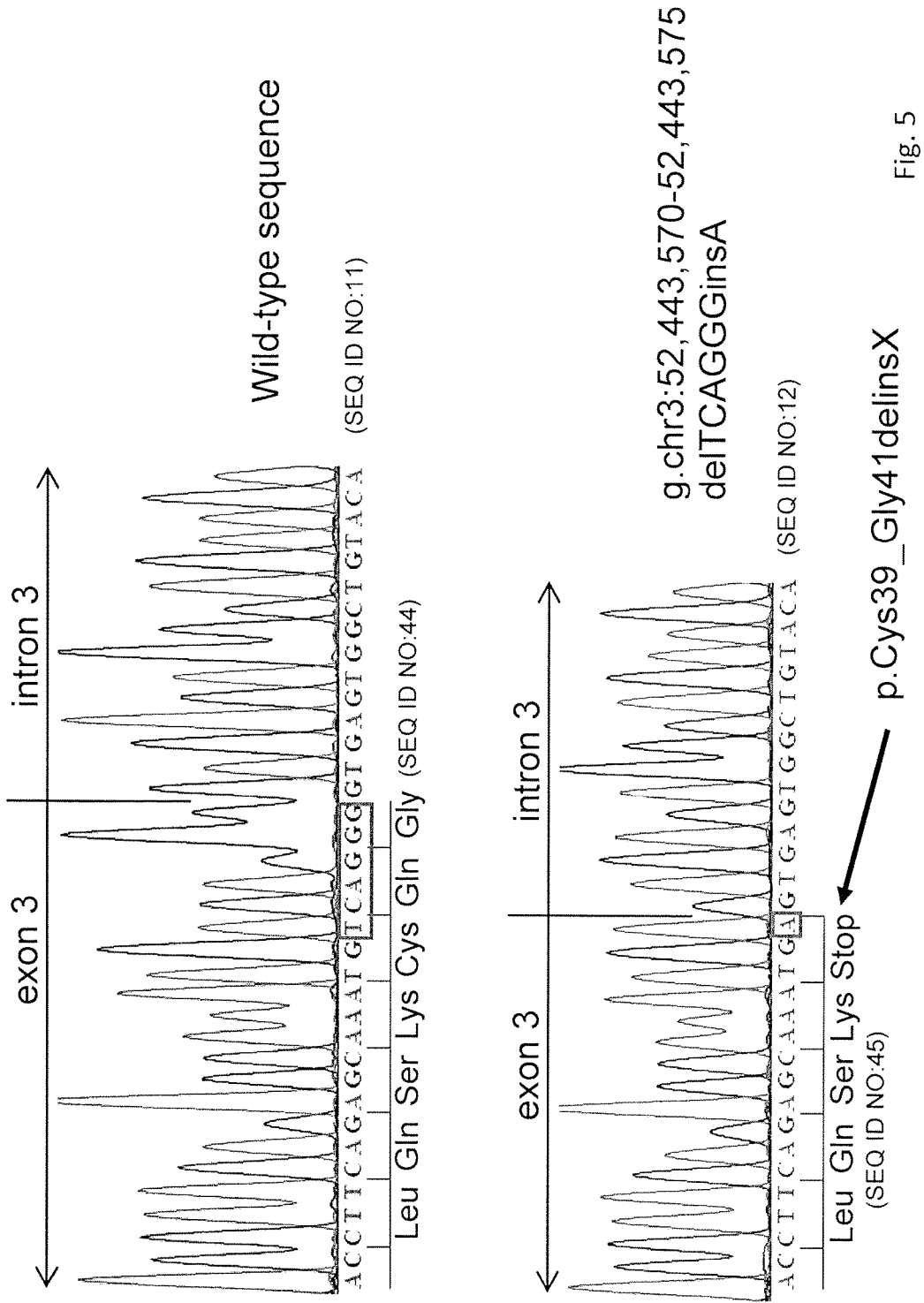

METHODS FOR DIAGNOSING A PREDISPOSITION TO DEVELOP CANCER

CROSS REFERENCE TO RELATED APPLICATIONS

This application is the U.S. National Phase of PCT No. PCT/US2012/025578, filed on Feb. 17, 2012, and claims priority to U.S. Provisional Application No. 61/444,438, filed on Feb. 18, 2011, and U.S. Provisional Application No. 61/524,959, filed on Aug. 18, 2011, the contents of each application are incorporated by reference herein, in their entirety and for all purposes.

STATEMENT OF GOVERNMENT SUPPORT

This invention was made with government support under Grant No. CA114047 awarded by the National Institutes of Health. The government has certain rights in the invention.

REFERENCE TO A SEQUENCE LISTING

This application includes a Sequence Listing submitted electronically as a text file named BAP1 PCT Sequence Listing_ST25.txt, created on Jan. 23, 2012, with a size of 16,000 bytes. The Sequence Listing is incorporated by reference herein.

FIELD OF THE INVENTION

The invention relates generally to the field of cancer diagnostics. More particularly, the invention relates to methods for diagnosing a predisposition to develop a cancer such as malignant mesothelioma. The invention also relates to arrays, systems, polynucleotides, and polypeptides, which may be used for practicing diagnostic methods.

BACKGROUND OF THE INVENTION

Various publications, including patents, published applications, accession numbers, technical articles and scholarly articles are cited throughout the specification. Each of these cited publications is incorporated by reference, in its entirety and for all purposes, in this document.

About 27 million US workers were exposed to asbestos between 1940 and 1979, and many more thereafter, and more than 30 million US homes contain asbestos. Presently, malignant mesothelioma causes about 3,000 deaths/year in the U.S. and about 5,000 in Western Europe. Despite asbestos abatement efforts, malignant mesothelioma rates have remained stable in the U.S. since 1994 and are expected to increase by 5-10% per year in most European countries for the next 25 years. With increased urban development, exposure may also occur from disturbing asbestos- and erionite-containing soil. Moreover, a dramatic increase in malignant mesothelioma incidence is predicted in developing countries, where use of asbestos is increasing.

In the United States, the annual incidence of malignant mesothelioma varies from 1-2/$10^6$ in states with minimal asbestos exposure to 10-15/$10^6$ in states where large quantities of asbestos have been used. The observation that only about 5% of workers exposed to high doses of asbestos developed malignant mesothelioma and the clustering of malignant mesothelioma in certain families suggests that genetics influences mineral fiber carcinogenesis.

With exposure to mineral fibers such as asbestos linked to malignant mesothelioma, and with exposure to mineral fibers continuing, it is important to identify risk factors that may predispose a subject to develop malignant mesothelioma, particularly when the subject is exposed to mineral fibers in the environment. A knowledge of such risk factors may provide for interventions that may delay or prevent the onset of malignant mesothelioma.

SUMMARY OF THE INVENTION

The invention features methods for identifying alterations in the germline BRCA1 associated protein 1 gene (BAP1) that predisposes a subject having the alteration to develop cancer, with the proviso that the alteration is not an insertion of an adenine between positions 1318 and 1319 of the BAP1 cDNA sequence of Genbank Accession No. NM_004656. One aspect of the methods comprises comparing the sequence of a nucleic acid encoding BAP1 determined from a tissue sample obtained from a subject with one or more reference nucleic acid sequences comprising one or more alterations in the wild type BAP1 germline sequence associated with predisposing a subject to develop cancer, and determining whether the determined sequence has the alteration based on the comparison. The comparing step may be carried out using a processor programmed to compare nucleic acid sequences.

One aspect of the methods comprises contacting a nucleic acid encoding BAP1 obtained from a subject with one or more polynucleotide probes having a nucleic acid sequence complementary to a BAP1 germline nucleic acid sequence having one or more alterations associated with predisposing a subject to develop cancer, and determining whether the one or more probes hybridized with the nucleic acid, for example, under stringent conditions. The hybridization may occur on a support such as an array, or in situ.

Methods for diagnosing a predisposition to develop cancer are provided. In some aspects, the methods comprise determining the sequence of a nucleic acid encoding BRCA1 associated protein 1 (BAP1) obtained from a subject, comparing the determined sequence with one or more reference sequences comprising one or more nucleic acid sequences comprising one or more alterations in the wild type BAP1 germline sequence associated with predisposing a subject to develop cancer, with the proviso that the alteration is not an insertion of an adenine between positions 1318 and 1319 of the BAP1 cDNA sequence of Genbank Accession No. NM_004656, using a processor programmed to compare determined sequences and reference sequences, and diagnosing whether the subject has a predisposition to develop cancer based on the comparison.

In some aspects, the methods comprise contacting a nucleic acid encoding BAP1 obtained from a subject with one or more polynucleotide probes having a nucleic acid sequence complementary to a BAP1 germline nucleic acid sequence having one or more alterations associated with predisposing a subject to develop cancer, with the proviso that the alteration is not an insertion of an adenine between positions 1318 and 1319 of the BAP1 cDNA sequence of Genbank Accession No. NM_004656, determining whether the one or more probes hybridized with the nucleic acid, for example, under stringent conditions, optionally, identifying which of the one or more probes hybridized with the nucleic acid, and diagnosing whether the subject has a predisposition to develop cancer based on the determination of whether the probes hybridized with the nucleic acid. The probes may comprise a detectable label. Optionally, the methods may comprise treating the subject with a regimen capable of inhibiting the onset of the cancer.

Isolated polynucleotides comprising a nucleic acid sequence, and the complement thereof, encoding the BAP1 protein and having at least one alteration that predisposes a subject to develop cancer, with the proviso that the alteration is not an insertion of an adenine between positions 1318 and 1319 of the BAP1 cDNA sequence of Genbank Accession No. NM_004656, are provided. The polynucleotides may be a probe. The polynucleotides may comprise a detectable label. The polynucleotides may be affixed to a support. An array comprising a plurality of polynucleotides are also provided. Polypeptides encoded by the polynucleotides are also provided.

Systems for diagnosing a predisposition to develop cancer comprise a data structure comprising one or more reference nucleic acid sequences having one or more alterations in the germline BAP1 nucleic acid sequence associated with predisposing a subject to develop cancer, with the proviso that the alteration is not an insertion of an adenine between positions 1318 and 1319 of the BAP1 cDNA sequence of Genbank Accession No. NM_004656, and a processor operably connected to the data structure. The processor may be a programmable processor, and may be capable of comparing nucleic acid sequences. The processor may comprise a network connection. Computer readable media comprise executable code for causing a programmable processor to compare nucleic acid sequences of BAP1-encoding nucleic acids obtained from a subject with reference nucleic acid sequences.

Methods for inhibiting the onset of cancer in a subject having one or more alterations in the BAP1 germline sequence that predispose a subject to develop cancer, with the proviso that the alteration is not an insertion of an adenine between positions 1318 and 1319 of the BAP1 cDNA sequence of Genbank Accession No. NM_004656, comprise one or more of restoring the wild type germline nucleic acid sequence of the BAP1 gene in the subject, administering to the subject an effective amount of wild type BAP1 protein, and/or reducing or eliminating exposure of the subject to carcinogenic mineral fibers such as asbestos and erionite.

BRIEF DESCRIPTION OF THE DRAWINGS

FIG. 1 shows pedigrees of two families (W and L) with high incidence of malignant mesothelioma (MM). Pedigrees showing family members with a germline mutation in BAP1, as confirmed by both sequencing and linkage analyses (III-04, III-06, III-08, III-09, IV-17, IV-21, II-12, II-05, III-31, III-18, III-22) or by linkage analysis alone (i.e., no DNA was available for sequencing)(II-02, III-10, II-14, II-03, II-07, III-15); individuals without the mutation (II-01, III-01, III-03, II-02, III-20) and individuals for whom DNA was unavailable (I-02, I-01, II-18, II-19) are also shown. Presence or absence of germline BAP1 mutation is also indicated with + or − symbols, respectively.

FIG. 2 shows array-CGH (comparative genomic hybridization) analysis of two families with familial MM, and a splicing assay performed on DNA continuing the mutation seen in family W.

FIG. 3 shows immunohistochemistry on mesotheliomas from L and W families revealing lack of BAP1 nuclear expression and only weak, focal cytoplasmic BAP1 staining. FIG. 3A shows SP-024, sporadic mesothelioma with wild-type BAP1; note the normal nuclear expression of BAP1. FIG. 3B shows W-III-06, FIG. 3C shows L-III-18, and FIG. 3D shows W-III-06, representing mesotheliomas from patients with germline BAP1 mutations: note lack of nuclear expression and weak cytoplasmic staining. All magnifications 400×. Bar=100 μm.

FIG. 4 shows BAP1 truncating mutations and aberrant protein expression in sporadic mesothelioma tumor biopsies.

FIG. 5 shows an electropherogram showing a possible germline BAP1 mutation observed in another family (not family W or L). The deletion/insertion mutation occurred at the end of exon 3, leading to a nonsense mutation (g.chr3: 52,443,570-52,443,575 delTCAGGGinsA). The mutation causes a premature truncation of the BAP1 protein at the amino terminus.

DETAILED DESCRIPTION OF THE INVENTION

Figure 1A:
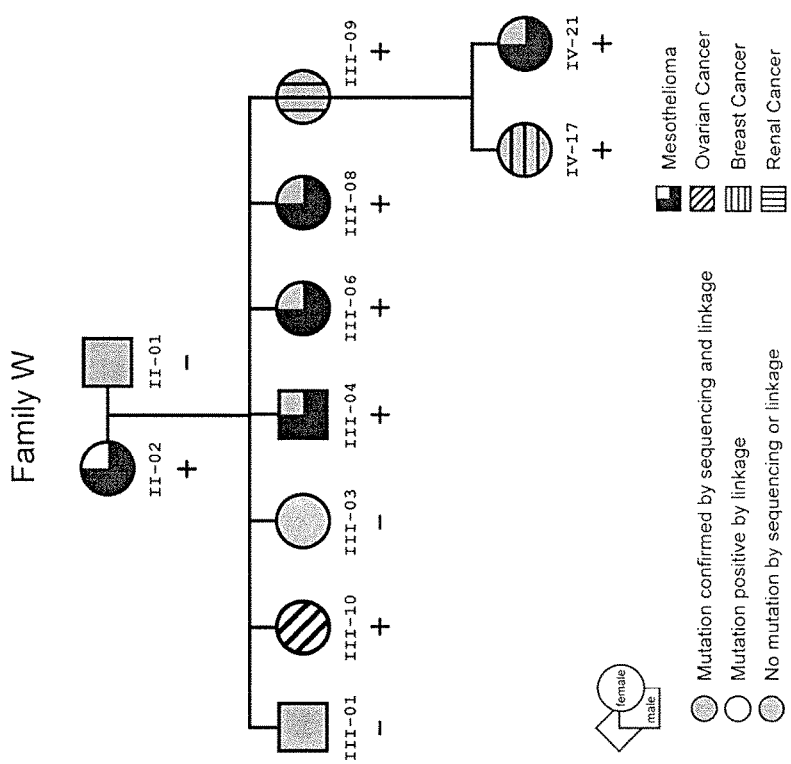
FIG. 1A shows a pedigree of family W, having 8 affected family members with cancer, including 5 with MM, indicating the presence or absence of germline mutation at BAP1 consensus splice acceptor site.

Various terms relating to aspects of the present invention are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

The terms subject and patient are used interchangeably throughout. A subject may be any animal, including mammals such as companion animals, laboratory animals, and non-human primates. Human beings are preferred.

A molecule such as a polynucleotide has been "isolated" if it has been removed from its natural environment and/or altered by the hand of a human being.

Wild type includes that which is naturally-occurring, normal, or non-mutated.

It has been observed in accordance with the invention that certain mutations, which include deletions, substitutions, rearrangements, and combinations thereof, in the germline nucleic acid sequence of the BRCA1 associated protein 1 (BAP1) gene predispose subjects having such mutations to develop cancer. In particular, it is believed that subjects having such germline mutations are predisposed to develop malignant mesothelioma, and it is believed that such subjects are predisposed to develop other cancers such as breast cancer, ovarian cancer, pancreatic cancer, kidney cancer, or skin cancer, including uveal melanoma. It is believed that subjects having mutations in the germline sequence of BAP1 may be considered as having a cancer predisposition syndrome such that they are at risk of developing any one of a number of these or other cancers. For example, it is believed that such subjects may have a predisposition to develop a mesothelioma-melanoma syndrome. It is believed that malignant mesothelioma may dominate in cases where such subjects are exposed to carcinogenic mineral fibers in the environment. Accordingly, the invention features methods for identifying germline nucleic acid sequence alterations in BAP1 that predispose a subject to develop cancer, as well as methods for diagnosing predispositions to develop cancer. Any of the methods may be carried out in vivo, in vitro, or in situ.

In some aspects, methods for identifying an alteration in the germline BRCA1 associated protein 1 (BAP1) gene that predisposes a subject having the alteration to develop cancer relate to sequence comparisons. In some aspects, the methods generally comprise the steps of comparing the sequence of a nucleic acid encoding BAP1 obtained from a tissue sample obtained from a subject with one or more reference nucleic acid sequences comprising one or more alterations in the wild type BAP1 germline sequence that predispose a subject to develop cancer, and determining whether the BAP1 sequence obtained from the subject has the alteration based on the comparison. The comparing step may be carried out using a processor programmed to compare nucleic acid sequences, for example, to compare the nucleic acid sequences obtained from the subject and the reference nucleic acid sequences. The methods may optionally include the step of determining the sequence of the nucleic acid encoding BAP1 obtained from the subject.

From the subject, the tissue sample may be from any tissue in which genomic DNA or a genomic DNA sequence may be obtained. Non-limiting examples include blood and buccal tissue. The methods may include the step of obtaining the tissue sample, and may include the step of obtaining the nucleic acid. The nucleic acid may be any nucleic acid that has, or from which may be obtained, the germline nucleic acid sequence encoding the BAP1 protein, or the complement thereof, or any portion thereof. For example, the nucleic acid may be chromosomal or genomic DNA, may be mRNA, or may be a cDNA obtained from the mRNA. The sequence of the nucleic acid may be determined using any sequencing method suitable in the art.

In some aspects, the methods for identifying an alteration in the germline BRCA1 associated protein 1 (BAP1) gene that predisposes a subject having the alteration to develop cancer include hybridization assays. For example, the methods generally comprise determining one or more alterations associated with predisposing a subject to develop cancer in the germline sequence of a nucleic acid encoding BAP1 in a tissue sample obtained from a subject. In one detailed aspect, the methods comprise the steps of contacting the nucleic acid obtained from the subject with one or more polynucleotide probes that have a nucleic acid sequence complementary to a BAP1 germline nucleic acid sequence having one or more alterations that predispose a subject to develop cancer, and determining whether the one or more probes hybridized with the nucleic acid encoding BAP1.

The probes may comprise a detectable label. The nucleic acid obtained from a subject may be labeled with a detectable label. Detectable labels may be any suitable chemical label, metal label, enzyme label, fluorescent label, radiolabel, or combination thereof. The methods may comprise detecting the detectable label on probes hybridized with the nucleic acid encoding BAP1. The probes may be affixed to a support, such as an array. For example, a labeled nucleic acid obtained from a subject may be contacted with an array of probes affixed to a support. The probes may include any probes described or exemplified herein.

In another detailed aspect, the hybridization may be carried out in situ, for example, in a cell obtained from the subject. For example, determining the one or more alterations may comprise contacting the cell, or contacting a nucleic acid in the cell, with one or more polynucleotide probes comprising a nucleic acid sequence complementary to a BAP1 germline nucleic acid sequence having one or more alterations that predispose a subject to develop cancer and comprising a detectable label, and detecting the detectable label on probes hybridized with the nucleic acid encoding BAP1. Detectable labels may be any suitable chemical label, metal label, enzyme label, fluorescent label, radiolabel, or combination thereof.

In any of the hybridization assays, the probes may be DNA or RNA, are preferably single stranded, and may have any length suitable for avoiding cross-hybridization of the probe with a second target having a similar sequence with the desired target. Suitable lengths are recognized in the art as from about 20 to about 60 nucleotides optimal for many hybridization assays (for example, see the Resequencing Array Design Guide available from Affymetrix: http://www.affymetrix.com/support/technical/byproduct.affx?product=cseq), though any suitable length may be used, including shorter than 20 or longer than 60 nucleotides. It is preferred that the probes hybridize under stringent conditions to the BAP1 germline nucleic acid sequence of interest. It is preferred that the probes have 100% complementary identity with the target sequence.

The methods described herein, including the hybridization assays, whether carried out in vitro, on an array, or in situ, may be used to determine any alteration in the BAP1 germline nucleic acid sequence that has a known or suspected association with predisposing a subject to develop cancer, including any of those described or exemplified herein. In any of the methods described herein, the alterations may be, for example, a mutation in the germline nucleic acid sequence. The mutation may comprise one or more nucleotide substitutions, an addition of one or more nucleotides in one or more locations, a deletion of one or more nucleotides in one or more locations, an inversion or other DNA rearrangement, or any combination thereof. A substitution may, but need not, change the amino acid sequence of the BAP1 protein. Any number of substitutions, additions, or deletions of nucleotides are possible. The alteration may occur in an intron, an exon, or both, including an alteration at or proximal to an exon-intron splice site. The one or more alterations may be located in human chromosome 3, for example, at segment 3p21.1, and may be at a BAP1 locus in this segment. The alterations in the germline sequence preferably do not include an insertion of an A between positions 1318-1319 of the BAP1 cDNA as described by Harbour et al. (2010) Science 330:1410-3 (see, e.g., Genbank Accession No. NM_004656)(the inserted A becomes nucleotide 1319, moving the wild type nucleotide at position 1319 to position 1320 and generating a stop codon).

One non-limiting example of a particular alteration that may predispose a subject to develop cancer includes a C to T substitution in exon 16. The substitution may occur at position 52,436,624 of human chromosome 3. The substitution may occur in a polynucleotide comprising SEQ ID NO:9. The polynucleotide having the substitution may comprise SEQ ID NO:10, or a portion thereof. The substitution may occur in the polynucleotide at the position corresponding to position 16 of SEQ ID NOs:9 or 10. Thus, for example, in a polynucleotide comprising SEQ ID NO: 9 or 10, the substitution may occur in the polynucleotide in the SEQ ID NO: 9 or 10 portion and at the position corresponding to position 16 thereof.

One non-limiting example of a particular exon-intron splice site alteration that predisposes a subject to develop cancer includes an A to G substitution 2 nucleotides upstream of the 3' end of Intron 6. The A to G substitution may occur at position 52,441,334 of human chromosome 3. The A to G substitution may occur in a polynucleotide comprising SEQ ID NO:1. The polynucleotide having the A to G substitution may comprise SEQ ID NO:2, or a portion thereof. The substitution may occur in the polynucleotide at the position corresponding to position 16 of SEQ ID NOs:1 or 2. Thus, for example, in a polynucleotide comprising SEQ ID NO: 1 or 2 the substitution may occur in the polynucleotide in the SEQ ID NO: 1 or 2 portion and at the position corresponding to position 16 thereof. The A to G substitution may result in an aberrant splice site product lacking exon 7, which may comprise SEQ ID NO:8, or a portion thereof.

Another non-limiting example of a particular exon-intron splice site alteration that predisposes a subject to develop cancer includes and a deletion of 5 nucleotides plus a substitution of 1 nucleotide at the 3' end of Exon 3. The alterations may occur in a polynucleotide comprising SEQ ID NO:11. The deleted 5 nucleotides may occur among positions 52,443,570 to 52,443,575 (e.g., 52,443,570 to 52,443,574) of human chromosome 3, may comprise SEQ ID NO:13, and may comprise the nucleotides corresponding to positions 17-21 of SEQ ID NO:11. The substitution may comprise an A to G substitution at the position corresponding to position 22 of SEQ ID NO:11, and may occur at position 52,443,575 of human chromosome 3. The resultant nucleic acid sequence may comprise SEQ ID NO:12, or a portion thereof.

Nucleotide deletions may occur any where in the germline BAP1 gene. In some aspects, the alteration comprises a deletion of a C in Exon 13. The deletion of the C may occur at position 52,437,444 of human chromosome 3. The gene comprising the deletion of the C may comprise SEQ ID NO:16. In some aspects, the alteration comprises a deletion of four nucleotides from Exon 14. The four nucleotides may comprise the sequence TCAC, and may occur at positions 52,437,159 to 52,437,162 of human chromosome 3. The deleted 4 nucleotides may comprise the nucleotides corresponding to positions 23-26 of SEQ ID NO:17. The gene comprising the deletion of TCAC may comprise SEQ ID NO:18.

One non-limiting example of a particular alteration that predisposes a subject to develop cancer, or that occurs as a somatic genetic change when a tumor forms, includes a deletion of 25 nucleotides in Exon 4. The deleted nucleotides may occur at positions 52,442,507 through 52,442,531 of human chromosome 3, may comprise SEQ ID NO:4, and may comprise the nucleotides corresponding to positions 17-41 of SEQ ID NO:3. The resultant nucleic acid sequence may comprise SEQ ID NO:5, or a portion thereof.

The reference nucleic acid sequences used in nucleic acid sequence comparison aspects may comprise one or more of SEQ ID NO:2, SEQ ID NO:4, SEQ ID NO:5, SEQ ID NO:8, SEQ ID NO: 10, SEQ ID NO:12, and SEQ ID NO:13, or portion thereof having the variation from the wild type sequence. The reference nucleic acid sequences may also include wild type nucleic acid sequences to serve as controls in the comparison, or for determinations that the subject does not have a germline nucleic acid sequence alteration that predisposes to develop cancer. Non-limiting examples of wild type nucleic acid sequences include SEQ ID NO:1, SEQ ID NO:3, SEQ ID NO:6, SEQ ID NO:7, SEQ ID NO:9, and SEQ ID NO:11. Reference nucleic acid sequences having any portion of the sequence of these sequence identifiers may be used.

The polynucleotide probes used in nucleic acid hybridization aspects may comprise one or more of SEQ ID NO:2, SEQ ID NO:4, SEQ ID NO:5, SEQ ID NO:8, SEQ ID NO: 10, SEQ ID NO:12, and SEQ ID NO:13, or portion thereof having the variation from the wild type sequence. The nucleic acid sequence of the probes may be complementary to SEQ ID NOs:2, 4, 5, 8, 10, 12, or 13. Polynucleotide probes having a wild type nucleic acid sequence may be used to serve as controls in hybridization assays, or for determinations that the subject does not have a germline nucleic acid sequence alteration that predisposes to develop cancer. Non-limiting examples of wild type nucleic acid sequences include SEQ ID NO:1, SEQ ID NO:3, SEQ ID NO:6, SEQ ID NO:7, SEQ ID NO:9, and SEQ ID NO:11. The nucleic acid sequence of the probes may be complementary to SEQ ID NOs:1, 3, 6, 7, 9, or 11. Probes having any portion of the sequence of these sequence identifiers, or complement thereof, may be used.

The methods for identifying an alteration in a germline BAP 1 nucleic acid sequence may be used in accordance with any alteration in the germline that predisposes a subject to develop any cancer. The cancer may be breast cancer, ovarian cancer, pancreatic cancer, kidney cancer, or skin cancer, including uveal melanoma, and/or malignant mesothelioma. Malignant mesothelioma is preferred. The alteration may predispose a subject to develop malignant mesothelioma upon exposure of the subject to a sufficient amount of mineral fibers, for example carcinogenic mineral fibers such as asbestos, erionite, refractory ceramic fibers, nanotubes, and other carcinogenic mineral fibers in the environment.

The invention also features methods for diagnosing a predisposition to develop cancer. In general, the diagnostic methods relate to the screening methods described above. In one aspect, the methods for diagnosing comprise the steps of determining the sequence of a nucleic acid encoding BAP1 obtained from a tissue sample obtained from a subject, comparing the determined sequence with one or more reference sequences comprising one or more alterations in the wild type BAP1 germline sequence that predispose a subject to develop cancer, and diagnosing the subject as having or not having a predisposition to develop cancer based on the comparison. Optionally, the one or more reference sequences may include one or more wild type BAP1 germline nucleic acid sequences. The comparing step may be carried out using a processor programmed to compare nucleic acid sequences, for example, the nucleic acid sequences determined from the subject and the reference nucleic acid sequences.

In one aspect, the methods for diagnosing comprise the steps of contacting a nucleic acid encoding BAP1 obtained from a tissue sample obtained from a subject with one or more polynucleotide probes comprising a nucleic acid sequence complementary to a BAP1 germline nucleic acid sequence having one or more alterations associated with predisposing a subject to develop cancer, determining whether the one or more probes hybridized with the nucleic acid, and diagnosing the subject as having or not having a predisposition to develop cancer based on the determination of whether the one or more probes hybridized with the nucleic acid. The methods may further comprise the steps of contacting a nucleic acid encoding BAP1 obtained from a tissue sample obtained from a subject with one or more reference polynucleotide probes having a nucleic acid sequence complementary to a wild type BAP1 germline nucleic acid sequence and determining whether the one or more reference polynucleotide probes hybridized with the nucleic acid. In cases where more than one probe (including reference probes) is contacted with the nucleic acid, the methods may further comprise the step of identifying which of the probes hybridized with the nucleic acid. The probes preferably hybridize to the BAP1 germline nucleic acid sequence under stringent conditions.

The hybridization may be carried out in vitro, and may be carried out using a support such as an array. For example, a nucleic acid obtained from a subject may be labeled and contacted with an array of probes affixed to a support. The probes may comprise DNA or RNA, and may comprise a detectable label. The hybridization may be carried out in situ, for example, in a cell obtained from the subject. For example, determining the one or more alterations may comprise contacting the cell, or contacting a nucleic acid in the cell with one or more polynucleotide probes comprising a nucleic acid sequence complementary to a BAP1 germline nucleic acid sequence having one or more alterations that predispose a subject to develop cancer and comprising a detectable label, and detecting the detectable label on probes hybridized with the nucleic acid. Detectable labels may be any suitable chemical label, metal label, enzyme label, fluorescent label, radiolabel, or combination thereof.

The methods for diagnosing, whether based on sequence comparison or probe hybridization, may further comprise the steps of treating the subject with a regimen capable of inhibiting the onset of the cancer. These steps may be included, for example, if it is determined that the subject has a predisposition to develop cancer.

The methods, whether based on sequence comparison or probe hybridization, may be used to diagnose a predisposition to any cancer, including one or more of breast cancer, ovarian cancer, pancreatic cancer, kidney cancer, skin cancer, including uveal melanoma, and malignant mesothelioma. The methods may be used to diagnose a predisposition to develop malignant mesothelioma upon exposure to a sufficient amount of mineral fibers in the environment, for example, asbestos or erionite. Thus, the treatment regimen may be tailored to inhibit the onset of one or more of such cancers. In some aspects, the treatment regimen comprises restoring the wild type germline nucleic acid sequence of BAP1 in the genomic DNA of the subject. In some aspects, the treatment regimen comprises administering to the subject an effective amount of wild type BAP1 protein. Alternatively, the treatment regimen may comprise modulating the expression or the biologic activity of a protein in a BAP1 cell signaling pathway whose expression or biologic activity is modulated by BAP1. In some aspects, the treatment regimen comprises administering to the subject an effective amount of a compound or pharmaceutical composition capable of delaying or inhibiting the onset of the cancer. In some aspects, the treatment regimen comprises one or more of diet management, vitamin supplementation, nutritional supplementation, exercise, psychological counseling, social counseling, education, and regimen compliance management. In some aspects, the treatment regimen comprises preventing, reducing, or eliminating exposure of the subject to mineral fibers such as asbestos, erionite, refractory ceramic fibers, or nanotubes. The treatment regimen may comprise targeting any imbalance in ubiquitination processes in susceptible tissues. The treatment regimen may comprise inhibiting RING1-dependent ubiquitination that normally counteracts the deubiquitinating activity of BAP1.

In the diagnostic methods, the tissue sample obtained from the subject may be from any tissue in which a genomic DNA sequence may be obtained. Non-limiting examples include blood and buccal tissue. The methods may include the step of obtaining the tissue sample, and may include the step of obtaining the nucleic acid. The nucleic acid may be any nucleic acid that has, or from which may be obtained, the germline nucleic acid sequence encoding the BAP1 protein, or the complement thereof, or any portion thereof. For example, the nucleic acid may be chromosomal or genomic DNA, may be mRNA, or may be a cDNA obtained from the mRNA.

The diagnoses are based on determining alterations in the germline BAP1 nucleic acid sequence that predispose a subject having such alterations to develop cancer, including any of the alterations described or exemplified herein. The reference nucleic acid sequences and the probes are thus based on alterations that predispose to develop cancer.

The alterations may be, for example, a mutation in the germline BAP1 nucleic acid sequence such as a substitution, an addition of one or more nucleotides in one or more locations, a deletion of one or more nucleotides in one or more locations, or any combination thereof. The alteration may occur in an intron, an exon, or both, including an alteration at or proximal to an exon-intron splice site. The one or more alterations may be located in human chromosome 3, for example, at segment 3p21, and may be at a BAP locus in this segment such as the BAP1 locus in 3p21.1. The alterations in the germline sequence preferably do not include an insertion of an A between positions 1318-1319 of the BAP1 cDNA as described by Harbour et al. (2010) Science 330:1410-3 (see, e.g., Genbank Accession No. NM_004656; SEQ ID N0:41)(the inserted A becomes nucleotide 1319, moving the wild type nucleotide at position 1319 to position 1320 and generating a stop codon; SEQ ID NO:42).

One non-limiting example of a particular alteration that predisposes a subject to develop cancer includes a C to T substitution in Exon 16. The substitution may occur at position 52,436,624 of human chromosome 3. The substitution may occur in a polynucleotide comprising SEQ ID NO:9. The polynucleotide having the substitution may comprise SEQ ID N0:10, or a portion thereof. The substitution may occur in the polynucleotide at the position corresponding to position 16 of SEQ ID NOs:9 or 10.

One non-limiting example of a particular exon-intron splice site alteration that predisposes a subject to develop cancer includes an A to G substitution 2 nucleotides upstream of the 3' end of Intron 6. The A to G substitution may occur at position 52,441,334 of human chromosome 3. The A to G substitution may occur in a polynucleotide comprising SEQ ID N0:1. The polynucleotide having the A to G substitution may comprise SEQ ID N0:2, or a portion thereof. The substitution may occur in the polynucleotide at the position corresponding to position 16 of SEQ ID NOs:1 or 2. The A to G substitution may result in an aberrant splice site product lacking exon 7, which may comprise SEQ ID NO:8, or a portion thereof.

Another non-limiting example of a particular exon-intron splice site alteration that predisposes a subject to develop cancer includes and a deletion of 5 nucleotides plus a substitution of 1 nucleotide at the 3' end of Exon 3. The alterations may occur in a polynucleotide comprising SEQ ID NO:11. The deleted 5 nucleotides may occur at positions 52,443,570 to 52,443,575 of human chromosome 3, may comprise SEQ ID NO:13, and may comprise the nucleotides corresponding to positions 17-21 of SEQ ID NO:11. The substitution may comprise an A to G substitution at the position corresponding to position 22 of SEQ ID NO:11. The resultant nucleic acid sequence may comprise SEQ ID NO:12, or a portion thereof.

Nucleotide deletions may occur any where in the germline BAP1 gene. In some aspects, the alteration comprises a deletion of a C in Exon 13. The deletion of the C may occur at position 52,437,444 of human chromosome 3. In some aspects, the alteration comprises a deletion of four nucleotides from Exon 14. The four nucleotides may comprise the sequence TCAC, and may occur at positions 52,437,159 to 52,437,162 of human chromosome 3.

One non-limiting example of a particular alteration that predisposes a subject to develop cancer includes a deletion of 25 nucleotides in Exon 4. The deleted nucleotides may occur at positions 52,442,507 through 52,442,531 of human chromosome 3, may comprise SEQ ID NO:4, and may comprise the nucleotides corresponding to positions 17-41 of SEQ ID NO:3. The resultant nucleic acid sequence may comprise SEQ ID NO:5, or a portion thereof.

The reference nucleic acid sequences used in nucleic acid sequence comparison aspects may comprise one or more of SEQ ID NO:2, SEQ ID NO:4, SEQ ID NO:5, SEQ ID NO:8, SEQ ID NO: 10, SEQ ID NO:12, and SEQ ID NO:13, or portion thereof having the variation from the wild type sequence. The reference nucleic acid sequences may also include wild type nucleic acid sequences to serve as controls in the comparison, or for determinations that the subject does not have a germline nucleic acid sequence alteration that predisposes to develop cancer. Non-limiting examples of wild type nucleic acid sequences include SEQ ID NO:1, SEQ ID NO:3, SEQ ID NO:6, SEQ ID NO:7, SEQ ID NO:9, and SEQ ID NO:11. Reference nucleic acid sequences having any portion of the sequence of these sequence identifiers may be used.

The polynucleotide probes used in nucleic acid hybridization aspects may comprise one or more of SEQ ID NO:2, SEQ ID NO:4, SEQ ID NO:5, SEQ ID NO:8, SEQ ID NO: 10, SEQ ID NO:12, and SEQ ID NO:13, or portion thereof having the variation from the wild type sequence. The nucleic acid sequence of the probes may be complementary to SEQ ID NOs:2, 4, 5, 8, 10, 12, or 13. Polynucleotide probes having a wild type nucleic acid sequence may be used to serve as controls in hybridization assays, or for determinations that the subject does not have a germline nucleic acid sequence alteration that predisposes to develop cancer. Non-limiting examples of wild type nucleic acid sequences include SEQ ID NO:1, SEQ ID NO:3, SEQ ID NO:6, SEQ ID NO:7, SEQ ID NO:9, and SEQ ID NO:11. The nucleic acid sequence of the probes may be complementary to SEQ ID NOs:1, 3, 6, 7, 9, or 11. Probes having any portion of the sequence of these sequence identifiers, or complement thereof, may be used.

The invention also provides isolated polynucleotides comprising a germline nucleic acid sequence encoding the BAP1 protein and having one or more alterations that predispose a subject to develop cancer. The invention also provides isolated polynucleotides comprising a probe having a nucleic acid sequence complementary to a BAP1 germline nucleic acid sequence having one or more alterations that predispose a subject to develop cancer. Probes may have any number of nucleotide bases. The one or more alterations may be any of the alterations described or exemplified herein.

Polynucleotides include polyribonucleotides and polydeoxyribonucleotide, which may be unmodified RNA or DNA or modified RNA or DNA, and include single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. Polynucleotides may have triple-stranded regions comprising RNA or DNA or both RNA and DNA, modified bases, unusual bases such as inosine, modified backbones, and enzymatic or metabolic modifications.

The alterations may comprise, for example, a mutation in the germline BAP1 nucleic acid sequence such as a substitution, an addition of one or more nucleotides in one or more locations, a deletion of one or more nucleotides in one or more locations, or any combination thereof. The alteration may occur in an intron, an exon, or both, including an alteration at or proximal to an exon-intron splice site. The one or more alterations may be located in human chromosome 3, for example, at segment 3p21, and may be at a BAP locus in this segment such as the BAP1 locus in 3p21.1. The alterations in the germline sequence preferably do not include an insertion of an A between positions 1318-1319 of the BAP1 cDNA as described by Harbour et al. (2010) Science 330:1410-3 (see, e.g., Genbank Accession No. NM_004656) (the inserted A becomes nucleotide 1319, moving the wild type nucleotide at position 1319 to position 1320 and generating a stop codon).

An alteration that predisposes a subject to develop cancer may comprise a C to T substitution in Exon 16. The substitution may occur at position 52,436,624 of human chromosome 3. The polynucleotide may comprise the nucleic acid sequence of SEQ ID NO:9, or the complement thereof, or a portion thereof. The polynucleotide may comprise the nucleic acid sequence of SEQ ID NO:10, or the complement thereof, or a portion thereof. For detection of the mutation, the polynucleotide preferably has at least about 95%, and more preferably 100% sequence identity with the nucleic acid sequence of SEQ ID NO:9, or the complement thereof. For detection of the mutation, the polynucleotide preferably has at least about 95%, and more preferably 100% sequence identity with the nucleic acid sequence of SEQ ID NO:10, or the complement thereof.

An exon-intron splice site alteration that predisposes a subject to develop cancer may comprise an A to G substitution 2 nucleotides upstream of the 3' end of Intron 6. The A to G substitution may occur at position 52,441,334 of human chromosome 3. The polynucleotide may comprise the nucleic acid sequence of SEQ ID NO:2, or the complement thereof, or a portion thereof. The polynucleotide may comprise the nucleic acid sequence of SEQ ID NO:1, or the complement thereof, or a portion thereof. The polynucleotide may comprise the nucleic acid sequence of SEQ ID NO:6, or the complement thereof, or a portion thereof. The polynucleotide may comprise the nucleic acid sequence of SEQ ID NO:7, or the complement thereof, or a portion thereof. The polynucleotide may comprise the nucleic acid sequence of SEQ ID NO:8, or the complement thereof, or a portion thereof. The polynucleotide may have at least about 95%, and more preferably 100% sequence identity with the nucleic acid sequence of SEQ ID NO:1, or the complement thereof. The polynucleotide may have at least about 95%, and more preferably 100% sequence identity with the nucleic acid sequence of SEQ ID NO:2, or the complement thereof. The polynucleotide may have at least about 95%, and more preferably 100% sequence identity with the nucleic acid sequence of SEQ ID NO:6, or the complement thereof. The polynucleotide may have at least about 95%, and more preferably 100% sequence identity with the nucleic acid sequence of SEQ ID NO:7, or the complement thereof. The polynucleotide may have at least about 95%, and more preferably 100% sequence identity with the nucleic acid sequence of SEQ ID N0:8, or the complement thereof.

An exon-intron splice site alteration that predisposes a subject to develop cancer may comprise a deletion of 5 nucleotides plus a substitution of 1 nucleotide at the 3' end of Exon 3. The deleted 5 nucleotides may occur among positions 52,443,570 to 52,443,575 of human chromosome 3. The polynucleotide may comprise the nucleic acid sequence of SEQ ID N0:3, or the complement thereof, or a portion thereof. The polynucleotide may comprise the nucleic acid sequence of SEQ ID N0:11, or the complement thereof, or a portion thereof. The polynucleotide may comprise the nucleic acid sequence of SEQ ID N0:12, or the complement thereof, or a portion thereof. The polynucleotide may have at least about 95% identity with the nucleic acid sequence of SEQ ID N0:11, or the complement thereof. The polynucleotide may have at least about 95%, and more preferably 100% sequence identity with the nucleic acid sequence of SEQ ID N0:12, or the complement thereof.

An alteration that predisposes a subject to develop cancer may comprise a deletion of 25 nucleotides in Exon 4. The deleted nucleotides may occur at positions 52,442,507 through 52,442,531 of human chromosome 3. The polynucleotide may comprise the nucleic acid sequence of SEQ ID N0:3, or the complement thereof, or a portion thereof. The polynucleotide may comprise the nucleic acid sequence of SEQ ID N0:4, or the complement thereof, or a portion thereof. The polynucleotide may comprise the nucleic acid sequence of SEQ ID N0:5, or the complement thereof, or a portion thereof. The polynucleotide may have at least about 95%, and more preferably 100% sequence identity with the nucleic acid sequence of SEQ ID N0:3, or the complement thereof. The polynucleotide may have at least about 95%, and more preferably 100% sequence identity with the nucleic acid sequence of SEQ ID N0:4, or the complement thereof. The polynucleotide may have at least about 95%, and more preferably 100% sequence identity with the nucleic acid sequence of SEQ ID N0:5, or the complement thereof.

The probes may comprise the nucleic acid sequence of SEQ ID N0:2, SEQ ID N0:4, SEQ ID N0:5, SEQ ID N0:8, SEQ ID NO: 10, or SEQ ID N0:12, or any portion of these sequences having the variation from the wild type sequence. The probes may comprise the complement of the nucleic acid sequence of SEQ ID N0:2, SEQ ID NO:4, SEQ ID NO:5, SEQ ID NO:8, SEQ ID NO: 10, or SEQ ID NO:12, or any portion of these sequences having the variation from the wild type sequence. The probes may comprise a detectable label. Detectable labels may be any suitable chemical label, metal label, enzyme label, fluorescent label, radiolabel, or combination thereof.

The invention also features a support comprising a plurality of polynucleotides comprising a germline nucleic acid sequence, or portion thereof, encoding the BAP1 protein or portion thereof, and having one or more alterations that predispose a subject to develop cancer, and optionally, a plurality of polynucleotides comprising a wild type germline nucleic acid sequence encoding the BAP1 protein. The support may comprise an array. The polynucleotides may be probes. The probes may comprise the nucleic acid sequence of SEQ ID NO:2, SEQ ID NO:4, SEQ ID NO:5, SEQ ID NO:8, SEQ ID NO: 10, or SEQ ID NO:12, or any portion of these sequences having the variation from the wild type sequence. The probes may comprise the complement of the nucleic acid sequence of SEQ ID NO:2, SEQ ID NO:4, SEQ ID NO:5, SEQ ID NO:8, SEQ ID NO: 10, or SEQ ID NO:12, or any portion of these sequences having the variation from the wild type sequence.

The invention also features isolated polypeptides, including isolated proteins comprising a polypeptide having an amino acid sequence encoded by a polynucleotide comprising a germline nucleic acid sequence encoding the BAP1 protein and having one or more alterations that predispose a subject to develop cancer. Polypeptides include polymers of amino acid residues, one or more artificial chemical mimetic of a corresponding naturally occurring amino acid, as well as to naturally occurring amino acid polymers and non-naturally occurring amino acid polymers. The polypeptides may comprise an amino acid sequence encoded by the nucleic acid sequence of SEQ ID NO:2, SEQ ID NO:4, SEQ ID NO:5, SEQ ID NO:8, SEQ ID NO: 10, or SEQ ID NO:12. Polypeptides include truncated BAP1 proteins, in which the truncation was caused by an alteration in the nucleic acid sequence encoding BAP1, which alteration is associated with a predisposition to develop cancer.

The invention also features systems for diagnosing a predisposition to develop cancer. In general, the systems comprise a data structure comprising one or more reference nucleic acid sequences having one or more alterations in the wild type BAP1 germline sequence associated with predisposing a subject to develop cancer, and a processor operably connected to the data structure. Optionally, the data structure may comprise one or more wild type reference nucleic acid sequences, which have a wild type BAP1 germline sequence. The processor is preferably capable of comparing, and preferably programmed to compare determined nucleic acid sequences (for example, those determined from nucleic acids obtained from a subject) with reference nucleic acid sequences, including wild type reference nucleic acid sequences.

The reference nucleic acid sequences may comprise the one or more alterations described or exemplified herein. The alterations may comprise, for example, a mutation in the germline nucleic acid sequence such as a substitution, an addition of one or more nucleotides in one or more locations, a deletion of one or more nucleotides in one or more locations, or any combination thereof. The alteration may occur in an intron, an exon, or both, including an alteration at or proximal to an exon-intron splice site. The one or more alterations may be located in human chromosome 3, for example, at segment 3p21, and may be at a BAP locus in this segment such as the BAP1 locus in 3p21.1. The alterations in the germline sequence preferably do not include an insertion of an A between positions 1318-1319 of the BAP1 cDNA as described by Harbour et al. (2010) Science 330: 1410-3 (see, e.g., Genbank Accession No. NM_004656; SEQ ID NO:41)(the inserted A becomes nucleotide 1319, moving the wild type nucleotide at position 1319 to position 1320 and generating a stop codon; SEQ ID NO:42).

Optionally, the system may comprise an input for accepting determined nucleic acid sequences obtained from tissue samples from a subject. Optionally, the system may comprise an output for providing results of a sequence comparison to a user such as the subject, or a technician, or a medical practitioner. Optionally, the system may comprise a sequencer for determining the sequence of a nucleic acid such as a nucleic acid obtained from a subject. Optionally, the system may comprise a detector for detecting a detectable label on a nucleic acid.

Optionally, the system may comprise computer readable media comprising executable code for causing a programmable processor to determine a diagnosis of the subject, for example whether the subject has a predisposition to develop a cancer such as breast cancer, ovarian cancer, pancreatic cancer, kidney cancer, skin cancer including uveal melanoma, or malignant mesothelioma, and/or a predisposition to develop malignant mesothelioma upon exposure to a sufficient amount of carcinogenic mineral fibers such as asbestos or erionite in the environment. The diagnosis may be based on the comparison of determined nucleic acid sequences with reference nucleic acid sequences. Thus, the system may comprise an output for providing a diagnosis to a user such as the subject, or a technician, or a medical practitioner. Optionally, the system may comprise computer readable media that comprises executable code for causing a programmable processor to recommend a treatment regimen for the subject, for example, a treatment regimen for preventing, inhibiting, or delaying the onset of a particular cancer, which cancer is preferably a cancer to which the subject is predisposed to develop on account of the presence of one or more alterations in the BAP1 germline nucleic acid sequence.

In any of the systems, a computer may comprise the processor or processors used for determining information, comparing information and determining results. The computer may comprise computer readable media comprising executable code for causing a programmable processor to determine a diagnosis of the subject. The systems may comprise a computer network connection, including an Internet connection.

The invention also provides computer-readable media. In some aspects, the computer-readable media comprise executable code for causing a programmable processor to compare the nucleic acid sequence of BAP1 determined from a nucleic acid obtained from a tissue sample obtained from a subject with one or more reference nucleic acid sequences having one or more alterations in the wild type BAP1 germline sequence associated with predisposing a subject to develop cancer. Optionally, the computer-readable media comprise executable code for causing a programmable processor to compare the nucleic acid sequence of BAP1 determined from a nucleic acid obtained from a tissue sample obtained from a subject with one or more wild type reference nucleic acid sequences having a wild type BAP1 germline sequence. The computer readable media may comprise a processor, which may be a computer processor.

The reference nucleic acid sequences may comprise any of the one or more alterations described or exemplified herein. The alterations may be, for example, a mutation in the germline nucleic acid sequence such as a substitution, an addition of one or more nucleotides in one or more locations, a deletion of one or more nucleotides in one or more locations, or any combination thereof. The alteration may occur in an intron, an exon, or both, including an alteration at or proximal to an exon-intron splice site. The one or more alterations may be located in human chromosome 3, for example, at segment 3p21.1, and may be at a BAP1 locus in this segment. The alterations in the germline sequence preferably do not include an insertion of an A between positions 1318-1319 of the BAP1 cDNA as described by Harbour et al. (2010) Science 330:1410-3 (see, e.g., Genbank Accession No. NM_004656; SEQ ID NO:41)(the inserted A becomes nucleotide 1319, moving the wild type nucleotide at position 1319 to position 1320 and generating a stop codon; SEQ ID NO:42).

The systems and computer readable media may be used in any of the methods described or exemplified herein, for example, methods for identifying alterations in the BAP1 gene, and methods for diagnosing a predisposition to develop cancer. For example, the systems and computer readable media may be used to facilitate comparisons of gene sequences, or to facilitate a diagnosis.

The invention also provides methods for inhibiting the onset of cancer in a subject having one or more alterations in the wild type germline BAP1 nucleic acid sequence that predispose a subject to develop cancer. The methods may be used to inhibit the onset of breast cancer, ovarian cancer, pancreatic cancer, kidney cancer, skin cancer including uveal melanoma, and/or malignant mesothelioma.

In one aspect, the methods comprise restoring the wild type germline nucleic acid sequence of BAP1 in the genomic DNA of the subject. The wild type germline nucleic acid sequence may be restored, for example, using any acceptable gene therapy technique. Restoring the wild type germline nucleic acid sequence may include, for example, reverting one or more alterations in the germline nucleic acid sequence to their wild type form. Reverting may include, for example, changing a substitution, adding back deleted nucleotides, or removing added nucleotides. The alterations may be those located to chromosome 3, and more particularly to chromosome segment 3p21, and preferably to the BAP1 locus in 3p21. The alterations may include the alterations described or exemplified herein.

In one aspect, the methods comprise administering to the subject an effective amount of wild type BAP1 mRNA or protein, or related mRNA or proteins along the BAP1 pathway. Preferably, the wild type BAP1 protein is active and is able to restore the normal biologic activity of BAP1 in the subject even in the presence of the defective BAP1 protein produced by the subject. Preferably, the wild type BAP1 protein is human BAP1 protein.

In one aspect, the methods comprise reducing or eliminating exposure of the subject to carcinogenic mineral fibers such as asbestos, erionite, refractory ceramic fibers, and nanotubes. For example, the subject may be counseled to avoid areas where carcinogenic mineral fibers are present naturally in the soil, or to avoid entering buildings, ships, and other structures where such mineral fibers are present in the building materials, or to avoid occupations that present a risk of exposure to such mineral fibers, such as asbestos removal occupations. The subject may be counseled to wear appropriate clothing or masks to avoid exposure to or inhalation of the mineral fibers.

The following examples are provided to describe the invention in greater detail. They are intended to illustrate, not to limit, the invention.

EXAMPLE 1

Experimental Methods

Samples. Blood and tumor samples were obtained following institutional review board guidelines of the University of Hawaii. Genomic copy number analysis, using Agilent 244K Genomic DNA arrays, were performed as described in Timakhov R A et al. (2009) Genes Chromosomes Cancer 48:786-94, and Altomare D et al. (2009) Proc. Natl. Acad. Sci. USA 106:3430-5. Cloning of genomic PCR products, DNA sequencing and Western blot analysis were carried out using standard procedures. Numbering of locations of mutations as shown in the figures, or describes above, is based on the February 2009 human reference sequence (GRCh37/hg19) (see the Santa Cruz Genome Browser http://genome.ucsc.edu/cgi-bin/hgGateway).

Genetic Linkage studies. All available family members were genotyped using the Affymetrix Genome-Wide Human SNP Array 6.0. Prior to linkage analyses, familial relationships were checked and corrected using PLINK. Parametric linkage analyses based on a 0.2 cM single nucleotide polymorphism (SNP) map assume a rare dominant model with age-dependent liability classes modeling the expected change in penetrance for different age groups. This platform contains nearly 2 million probes for SNPs and copy number variants (CNV). Genotyping performed on all samples together using the BIRDSEED version 2 algorithm provided genotypes for 909,623 SNPs for quality control analyses. PLINK was used to remove SNPs with a minor allele frequency below 5% in HapMap CEU samples (race matched), SNPs monomorphic in the data, and SNPs with less than perfect call rates. PLINK was also used to verify relationships in the pedigrees, by generating estimates for the proportion of SNPs inherited identical by descent (IBD) among family members.

Cloning and Sequence Analysis. Multiple PCR products encompassing the entire BAP1 coding exons, adjacent intron sequences, and 5' and 3' untranslated regions were PCR amplified for sequencing. To evaluate the splice acceptor site mutation seen in family W, a PCR-based strategy was used to clone genomic BAP1 sequences encompassing exons 4-8 and intervening introns, including the intron 6 splice mutation. Primers incorporated a XhoI restriction site at the 5' end and an EcoRI restriction site at the 3' end of the PCR product. Gel purified PCR products were cloned into pcDNA 3.1(-) plasmid (Invitrogen, Carlsbad, Calif.) using the two restriction sites. Individual clones were sequenced verified. Numbering of locations of mutations is based on the February 2009 human reference sequence (GRCh37/hg19).

DNA Copy Number Analysis. Oligonucleotide aCGH analysis was performed using 244K Human Genome CGH microarrays (G4411B) from Agilent Technologies (Santa Clara, Calif.). DNA (2-3 µg) from formalin-fixed, paraffin-embedded MM specimens was labeled using Agilent's Genomic DNA ULS Labeling Kit. ULS-Cy5- and ULS-Cy3-labeled DNA products were purified using Microcon YM-30 filtration devices. Appropriate ULS-Cy5- and ULS-Cy3-labeled DNA sample pairs were combined and mixed with human Cot-1 DNA, Agilent Blocking Agent and Hi-RPM Hybridization Buffer. Labeled target solution was hybridized to the microarray using SureHyb chambers. After hybridization and washing, microarrays were scanned using an Agilent microarray scanner. Data for individual features on the microarray were extracted from the scan image using Agilent's Feature Extraction (FE) Software. Output files were imported into Agilent's CGH data analysis software, DNA Analytics, for DNA copy number analysis. Western Blot Analysis. Total cellular protein from human malignant mesothelioma cell lines was isolated by using cell lysis buffer supplemented with 2 mM PMSF (Cell Signaling Technology, Danvers, Mass.). Cell lysates were incubated on ice for 15 min, and cell debris was removed by centrifuging at 15,000×g for 15 min at 4° C. Protein concentration was determined by the Bradford method (Bio-Rad, Hercules, Calif.). For immunoblotting, samples (50 µg) were separated by Tris-Glycine-buffered SDS-PAGE gel (Invitrogen, Carlsbad, Calif.) and transferred to polyvinylidene difluoride membranes (Millipore, Billerica, Mass.). Immunoblots were incubated with primary antibodies at 4° C. overnight, followed by incubation with secondary antibody conjugated with horseradish peroxidase for 60 min at room temperature. Antibodies against BAP1 and GAPDH were from Santa Cruz Biotechnology (Santa Cruz, Calif.). Tumor cell lines used for immunoblotting were established from surgically resected primary human mesothelioma specimens.

Clonogenic Assay. Human malignant mesothelioma cell lines ($2 \times 10^5$ cells) were seeded in 6-well plates and incubated at 37° C. overnight. Cells were transfected with 2 µg of wild-type BAP1 plasmid (OriGene, Rockville, Md.) or control vector by using Lipofectamine 2000 (Invitrogen).

Forty-eight hours after transfection, the cells were selected by culturing in culture medium containing 400 µg/mL G418 (Invitrogen). Two weeks after selection, colonies were stained with Diff-Quik stain (Dade Behring, Newark, Del.) and counted.

EXAMPLE 2

Experimental Results

Efforts were concentrated on two US MM-families, because it was possible to collect samples of interest from every member of these families. Moreover, members of these families were not occupationally exposed to asbestos nor exposed to erionite, thus removing the confounding factor of heavy exposure to a carcinogen known to cause MM. These two families had a high incidence of MM and various other cancers (FIG. 1A, B).

Samples from the ceiling, roof, tiles, driveways, and other surfaces of each of the houses where these families lived 20 or more years ago were collected and analyzed (MM latency is 20-60 years from initial exposure). Traces of chrysotile, but not amphibole asbestos, were found in 5/5 homes where the L family lived, and of tremolite and chrysotile in 1/1 home where all affected members of family W lived for several years. Since asbestos becomes airborne when materials containing asbestos are disturbed, it is possible that family members were exposed.

Figure 2A:
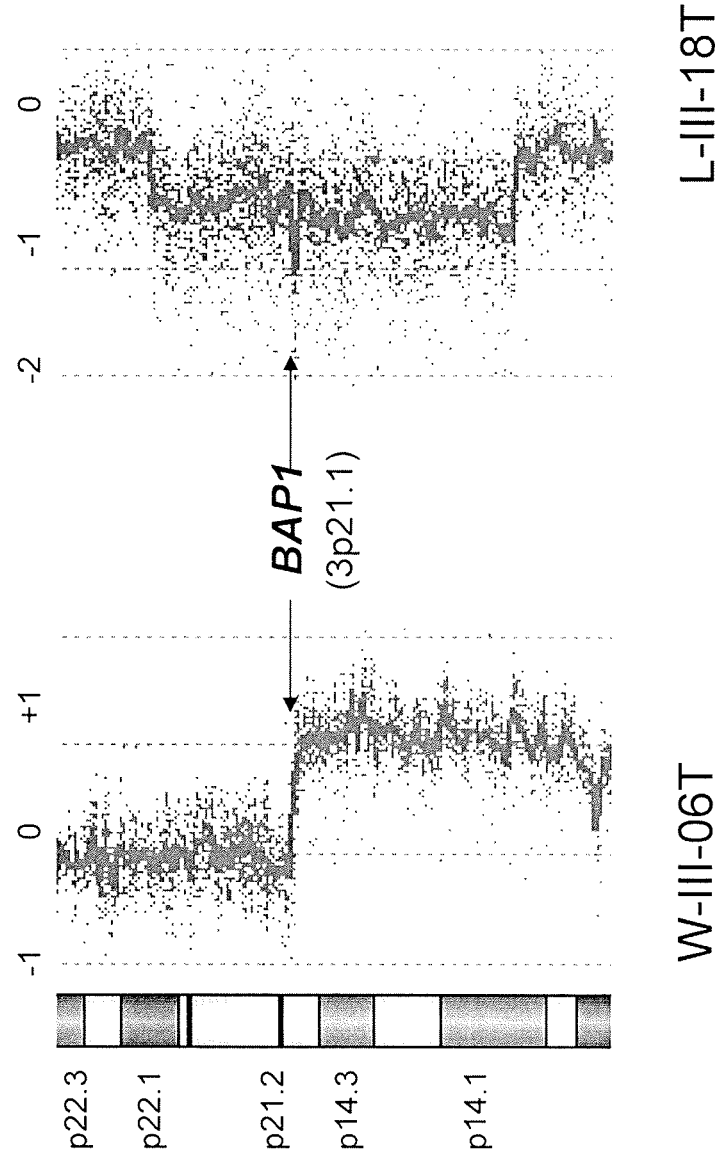
FIG. 2A shows the results of array-CGH analysis of MM from family W and another from family L with rearrangements affecting BAP1. Tumor L-III-18T had focal deletion encompassing BAP1 within larger 3p deletion, while tumor W-III-06T showed an amplification junction within BAP1.

Array-CGH analysis of two tumors (one per family) uncovered rearrangements affecting the BAP1 locus in 3p21.1. In one tumor (L-III-18T), a focal deletion encompassing BAP1 was seen within a larger deletion, while in the second (W-III-06T), an amplification junction occurred within the BAP1 locus (FIG. 2A).

The BAP1 gene in germline DNA from both families was sequenced, initially showing that six affected members (4 with MM; 2 with breast or renal cancer) examined from family W had the same inherited mutation, whereas 3 unaffected relatives did not (FIG. 1A). In addition, linkage analysis established that case W-III-10 (ovarian cancer) also has the mutated haplotype.

Figure 2B:
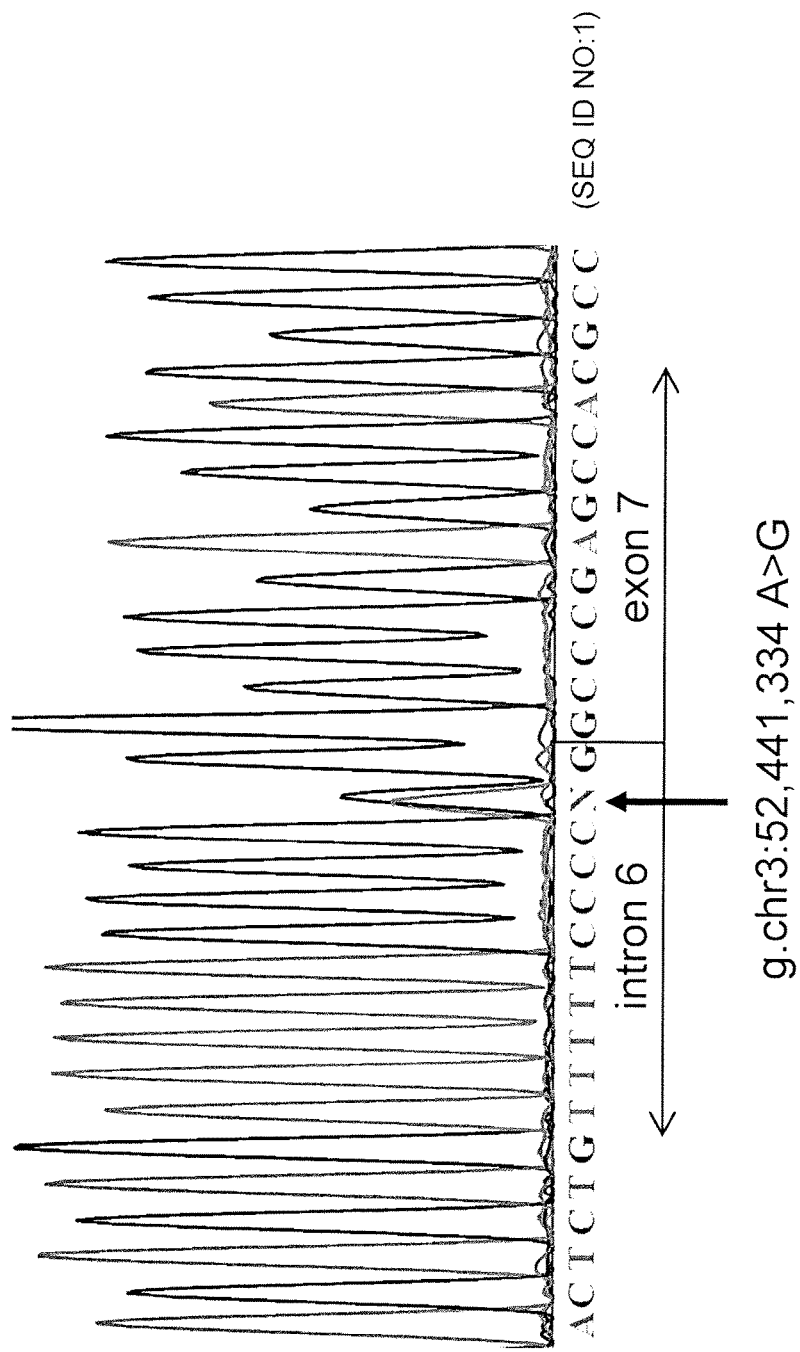
FIG. 2B shows an electropherogram depicting the heterozygous germline BAP1 splice site mutation in family W. The same mutation was present in germline of all other affected cases but absent in unaffected family members.
Figure 2C:
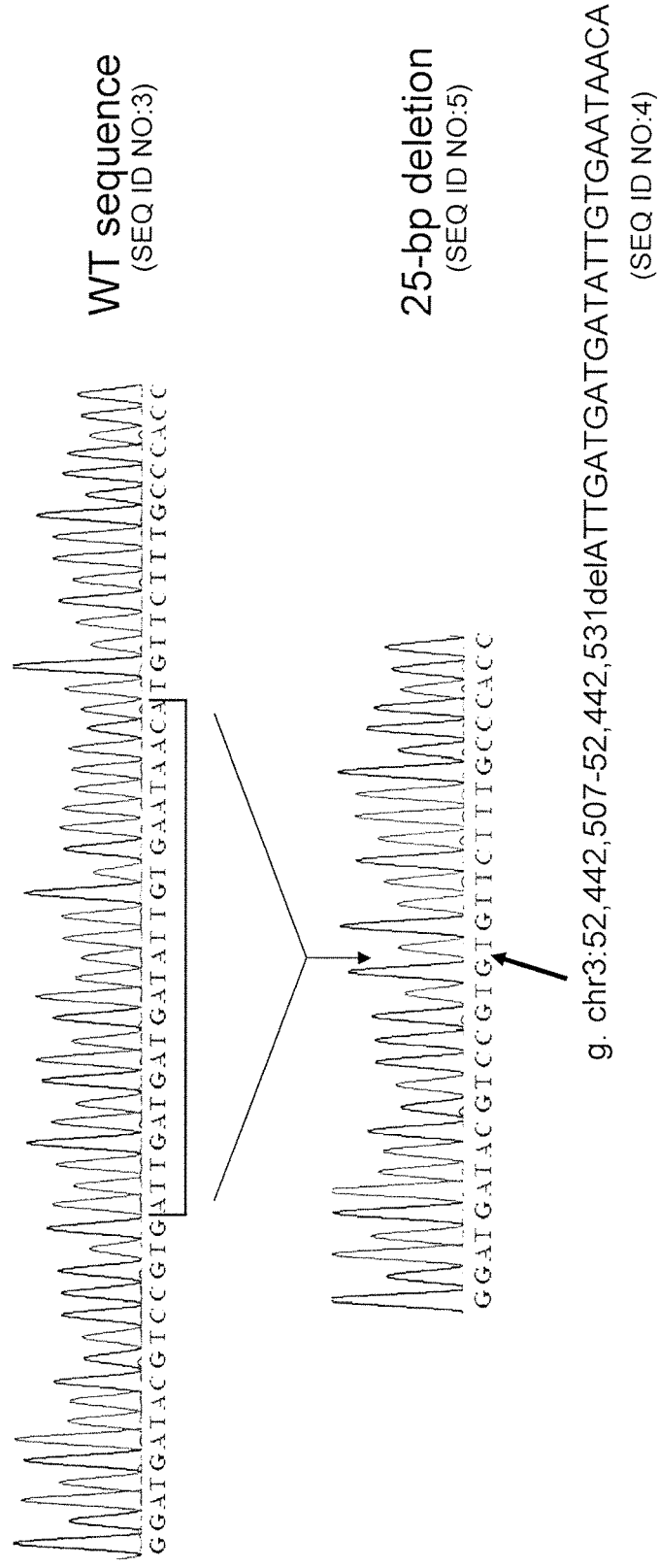
FIG. 2C shows an electropherogram of the 25-bp deletion within exon 4 of BAP1 in tumor W-III-04T. Most individual clones of PCR products of BAP1 genomic DNA contained either the somatic 25-bp deletion or the splice site mutation sequence, but not both. The deletion results in a frameshift and premature termination of BAP1.
Figure 2D:
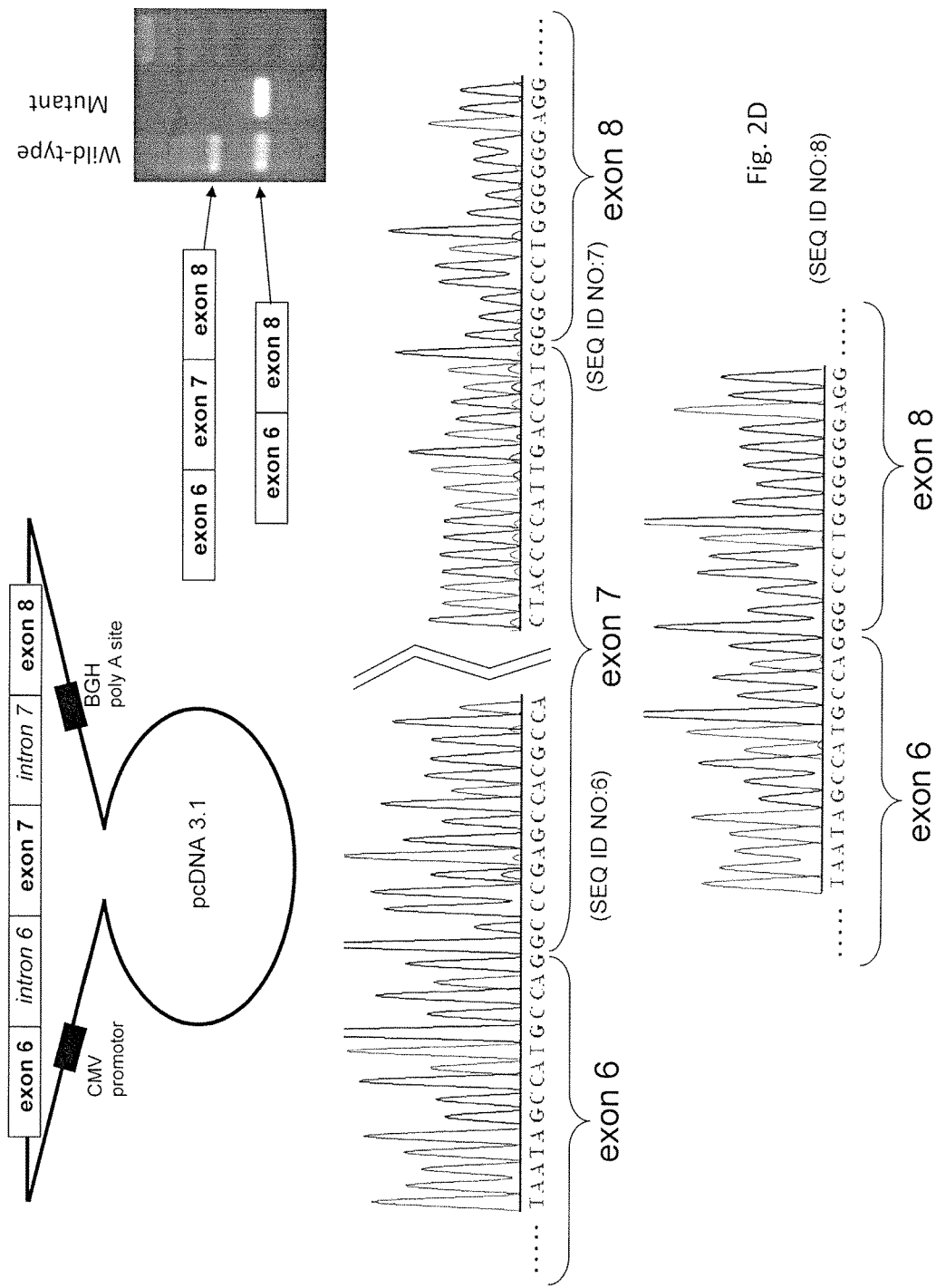
FIG. 2D shows a mini-gene expression construct used for the splicing assay (upper left). RT-PCR analysis revealed two BAP1 bands in 293T cells transfected with wild-type construct, but only the smaller band in cells transfected with mutant construct (upper right). Sequencing revealed that the larger band contained correctly spliced exons 6-8, while smaller band contained only exon 6 and exon 8 (bottom).

The mutation occurred at the intron 6/exon 7 boundary, with affected individuals having an A→G substitution at the −2 nucleotide consensus splice acceptor site (FIG. 2B). Such alterations often lead to exon skipping and pathogenic protein sequence changes. Tumor DNA was available in several cases, one of which (W-III-04T) showed a 25-bp deletion in exon 4 as well as the splice site mutation (FIG. 2C). The deletion resulted in a frameshift and premature termination of BAP1 (p.I72fsX7). Matched germline DNA did not contain the deletion, indicating that it was somatic in origin. Cloning of genomic PCR products encompassing exons 4-8 from tumor DNA suggested that the splice site mutation and deletion reside in different alleles, consistent with biallelic inactivation of BAP1. Transfection of mammalian cells with a genomic construct encompassing exons 6-8, and with the intron 6 splice site mutation, resulted in an aberrant splice product lacking exon 7 and a frameshift affecting the BAP1 nuclear ubiquitin carboxyl-terminal hydrolase (UCH) domain (FIG. 2D).

Figure 2E:
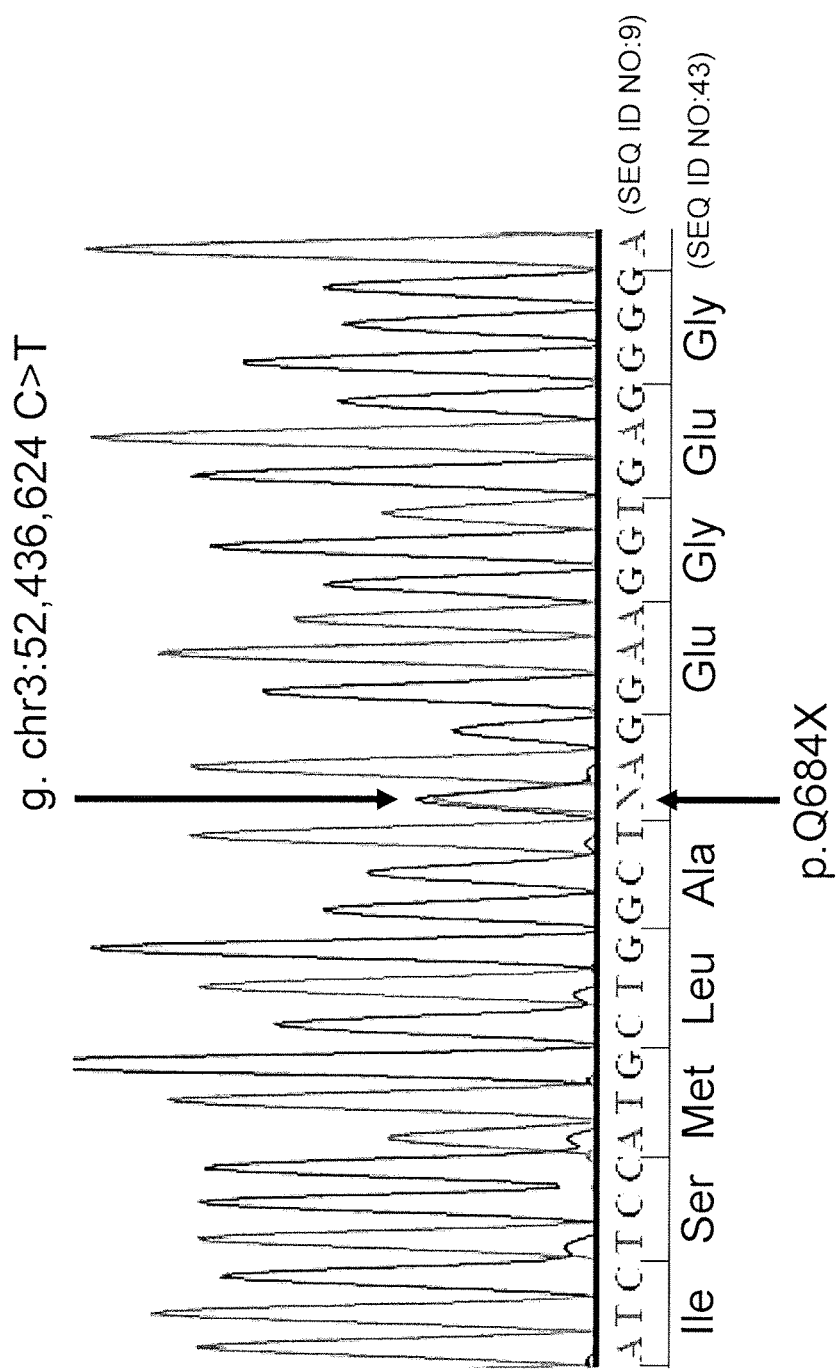
FIG. 2E shows an electropherogram depicting BAP1 nonsense mutation (g. chr3:52,436,624 C>T) observed in germline DNA of affected members of family L. The resulting CAG>TAG stop codon causes a premature truncation at the carboxy-terminus leading to loss of the nuclear localization signal.

In family L, germline DNA from 3 MMs, 2 uveal melanomas, and 2 skin cancers exhibited a germline C/G to T/A transition in exon 16, creating a premature termination codon (p.Q684X) (FIG. 2E). The nonsense mutation results in premature termination of the nuclear localization signal located in the carboxy-terminus of BAP1. BAP1 mutations were not detected in two family members with prostate cancer, were not detected in one family member with non-Hodgkin's lymphoma, and not detected in three healthy spouses. Linkage analyses revealed that case 11-03 (pancreatic cancer) was a mutation carrier.

Exome sequencing, using the Illumina HiSeq 2000 system, of germline DNA from two affected members of each family verified the splice site and nonsense mutations in family W and family L, respectively (not shown). Immunohistochemistry on mesotheliomas from L and W families revealed lack of BAP1 nuclear expression (FIG. 3).

Figure 4A:
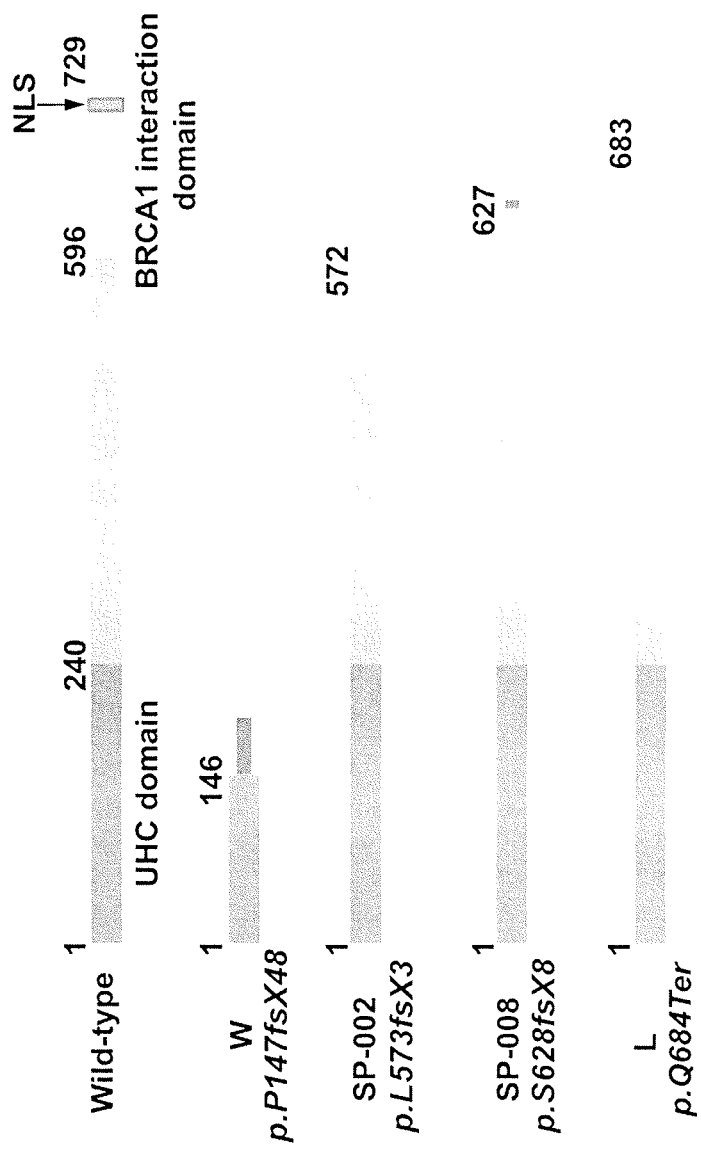
FIG. 4A shows a schematic diagram of predicted truncations of BAP1 in four sporadic mesotheliomas harboring BAP1 mutations. Bracket at left indicates mutations in two different BAP1 alleles in tumor sample SP-015. NLS, nuclear localization signal at carboxy-terminus of BAP1. Frameshift sequences are shown as thinner gray bars.
Figure 4B:
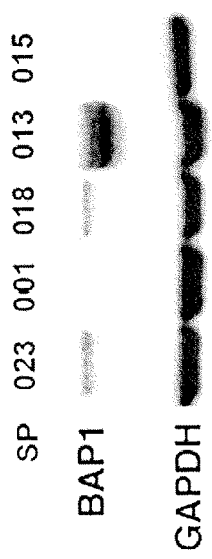
FIG. 4B shows an immunoblot analysis on whole tumor cell lysates of the same four sporadic mesotheliomas with somatic BAP1 mutations (lanes 2-5) and sporadic tumor lacking a BAP1 mutation (lane 1). Sporadic mesotheliomas with somatic BAP1 mutations show decreased expression of BAP1 compared to that seen in tumor without BAP1 mutation. Note that in mesotheliomas, whole tumor cell lysates inevitably contain some normal stromal cells that may be responsible for the faint BAP1 signal detected. Also note the presence of additional, faster-migrating BAP1 band in sample shown in lane 4 (SP-013), suggesting the presence of a truncated form of BAP1. The BAP1 protein products predicted in tumors SP-001 and SP-015 were not observed, suggesting nonsense-mediated mRNA decay. The mutation in tumor SP-018 results in a predicted protein product only 15 amino acids smaller, which presumably precludes detection of a small change in molecular weight compared to wild-type BAP1. GAPDH was used as a loading control.

Following the linking of BAP1 mutations to familial mesothelioma, BAP1 was sequenced (17 exons/introns/promoter) in 26 germline DNAs from sporadic mesothelioma patients. All of the patients had reported asbestos exposure to the treating physician, although these claims were not verified by lung content or mineralogical analyses. Two of 26 had BAP1 deletions: c.1832delC in exon 13 (p.P573fsX3) and c.2008-2011delTCAC in exon 14 (p.Y628fsX8) (Table 1). Both mutations result in a frameshift leading to a stop codon upstream of the region encoding the BAP1 nuclear localization signal (FIG. 2d). Upon an investigation as to whether anything was unique about these two patients, it was found that each had been treated for uveal melanoma 1 or 6 years before being diagnosed with mesothelioma. Of the remaining 24 sporadic mesotheliomas, none had uveal melanoma. Tumor DNA was available from 18 of the 26 sporadic mesothelioma patients: DNA sequencing revealed truncating BAP1 mutations in 4/18 (22%) tumors (FIG. 4A); BAP1 alterations in these tumors were supported by immunoblot analyses (FIG. 4B).

TABLE 1

Summary of genetic and demographic data of cases in this study

| Sample ID | Age[a] | Gender | MM | MM Histology | Uveal Melanoma | Other Cancers | Germline BAP1 Mutation | Mutations Identified in Mesothelioma Specimens |
|---|---|---|---|---|---|---|---|---|
| L-II-05 | 82a | F | No | | No | Squamous cell ca. (skin) | Exon 16 (52,436,624 C > T-nonsense) | |
| L-II-12 | 68a | F | No | | No | Basal cell ca. | Exon 16 (52,436,624 C > T-nonsense) | |
| L-II-18 | 54d | F | No | | Yes | Metastasis to liver | (no DNA available) | |
| L-II-09 | 65d | F | Yes | N.A. | None | None | (no DNA available) | |
| L-II-14 | 57d | M | Yes | N.A. | No | None | Exon 16 (52,436,624 C > T-nonsense)[b] | |
| L-II-03 | 73d | F | No | | No | Pancreatic ca. | Exon 16 (52,436,624 C > T-nonsense)[b] | |
| L-II-07 | 70d | F | Yes | N.A. | No | None | Exon 16 (52,436,624 C > T-nonsense)[b] | |

TABLE 1-continued

Summary of genetic and demographic data of cases in this study

| Sample ID | Age[a] | Gender | MM | MM Histology | Uveal Melanoma | Other Cancers | Germline BAP1 Mutation | Mutations Identified in Mesothelioma Specimens |
|---|---|---|---|---|---|---|---|---|
| L-III-18 | 59 | F | Yes | E | Yes | None | Exon 16 (52,436,624 C > T-nonsense) | Exon 16 (52,436,624 C > T-nonsense)[c] |
| L-III-22 | 63 | F | Yes | E | No | None | Exon 16 (52,436,624 C > T-nonsense) | N.D. |
| L-III-31 | 50 | M | Yes | E | No | None | Exon 16 (52,436,624 C > T-nonsense) | N.D. |
| L-II-02 | 86a | M | No | | No | Prostate ca. | None | |
| L-III-15 | 81a | F | Yes | N.A. | No | None | Exon 16 (52,436,624 C > T-nonsense)[b] | |
| L-III-20 | 59 | M | No | | No | Prostate ca | None | |
| W-III-04 | 58 | M | Yes | E | No | None | Intron 6 (52,441,334 A > G-splice site) | Intron 6 (52,441,334 A > G-splice site); Exon 4 (52,442,507-531 ATTGATGATGATATTGTGAATAACA del) (SEQ ID NO: 4) |
| W-III-06 | 50 | F | Yes | E | No | None | Intron 6 (52,441,334 A > G-splice site) | Intron 6 (52,441,334 A > G-splice site)[d] |
| W-III-08 | 58 | F | Yes | E | No | None | Intron 6 (52,441,334 A > G-splice site) | Intron 6 (52,441,334 A > G-splice site)[e] |
| W-IV-21 | 44 | F | Yes | E | No | None | Intron 6 (52,441,334 A > G-splice site) | N.D. |
| W-IV-17 | 37 | F | No | | No | Breast ca. | Intron 6 (52,441,334 A > G-splice site) | |
| W-III-09 | 57 | F | No | | No | Clear cell renal cell ca. | Intron 6 (52,441,334 A > G-splice site) | |
| W-II-01 | 92d | M | No | | No | None | None | |
| W-II-02 | 36 | F | Yes | N.A. | No | None | Intron 6 (52,441,334 A > G-splice site)[b] | |
| W-III-01 | 57a | M | No | | No | None | None | |
| W-III-03 | 59a | F | No | | No | None | None | |
| W-III-10 | 59 | F | No | | No | Ovarian ca. | Intron 6 (52,441,334 A > G-splice site)[b] | |
| SP-002 | 55 | F | Yes | E | Yes | Leiomyosarcoma | Exon 13 (52,437,444 C del) | N.D. |
| SP-008 | 63 | M | Yes | E | Yes | None | Exon 14 (52,437,159-162 TCAC del) | N.D. |
| SP-007 | 55 | F | Yes | E | No | Basal cell ca. | None | N.D. |
| SP-011 | 63 | M | Yes | B | No | Basal cell ca. | None | None |
| SP-015 | 82 | M | Yes | E | No | Basal cell ca. | None | Exon 9 (52,440,352 G del) Exon 13 (52,437,664 C del) |
| SP-026 | 66 | M | Yes | B | No | Basal cell ca. | None | None |
| SP-020 | 75 | M | Yes | E | No | Basal cell ca.; Meningioma | None | None |
| SP-025 | 52 | M | Yes | E | No | Basal cell ca.; Squamous cell ca. (skin) | None | None |
| SP-005 | 34 | F | Yes | E | No | Breast ca.; Leiomyosarcoma | None | N.D. |
| SP-010 | 69 | F | Yes | E | No | Breast ca.; Bronchioalveolar ca.; Pancreatic ca. | None | N.D. |
| SP-019 | 71 | M | Yes | B | No | Colon ca. | None | None |
| SP-016 | 74 | M | Yes | E | No | Colon ca.; Prostate ca. | None | None |
| SP-004 | 62 | F | Yes | B | No | Hairy cell leukemia | None | N.D. |
| SP-003 | 64 | M | Yes | E | No | Melanoma (skin) | None | N.D. |
| SP-017 | 74 | M | Yes | E | No | Melanoma (skin) | None | None |
| SP-018 | 70 | M | Yes | E | No | Prostate ca. | None | Exon 17 (52,436,398-399 CG del) |
| SP-013 | 70 | M | Yes | B | No | Prostate ca. | None | Exon 16 (52,436,599-627 GCTCAGGAAGGTGAGGGGATGCGCTG CTG del) (SEQ ID NO: 14) |
| SP-021 | 61 | M | Yes | E | No | Prostate ca. | None | None |
| SP-012 | 58 | F | Yes | E | No | Squamous cell ca. (skin) | None | None |
| SP-001 | 63 | M | Yes | E | No | None | None | Exon 11 (52,439,219 C del) |
| SP-006 | 60 | M | Yes | E | No | None | None | N.D. |
| SP-009 | 55 | M | Yes | E | No | None | None | None |
| SP-014 | 60 | M | Yes | E | No | None | None | None |
| SP-022 | 56 | M | Yes | E | No | None | None | None |

TABLE 1-continued

Summary of genetic and demographic data of cases in this study

| Sample ID | Age[a] | Gender | MM | MM Histology | Uveal Melanoma | Other Cancers | Germline BAP1 Mutation | Mutations Identified in Mesothelioma Specimens |
|---|---|---|---|---|---|---|---|---|
| SP-023 | 53 | F | Yes | B | No | None | None | None |
| SP-024 | 78 | M | Yes | B | No | None | None | None |

MM, malignant mesothelioma;
ca., carcinoma;
N.A., not available;
N.D., not determined;
E, epithelial MM histology;
del, deletion;
B, biphasic MM histology.
[a]Age at diagnosis. When this information was not available, either current age of patient who is still alive (e.g., 82a) or age at death (e.g., 92d) are indicated.
[b]Presence of mutation inferred based on the results of linkage analysis; all others were determined by DNA sequencing.
[c]An aCGH analysis revealed a focal homozygous deletion (~218 kb in size) encompassing the entire BAP1 locus, indicating that at least a subset of tumor cells have loss of both mutant and wild-type BAP1 alleles.
[d]aCGH analysis showed amplicon within 4 kb of BAP1 locus.
[e]DNA sequencing revealed absence of wild-type BAP1 allele Germline DNA from one member of a family not from family W or family L had a 6-bp deletion in exon 3, which occurred in tandem with the substitution of a single nucleotide. With the substitution, there was a net loss of 5 bases. This dual alteration created a premature stop codon (FIG. 5).

Figure 6A:
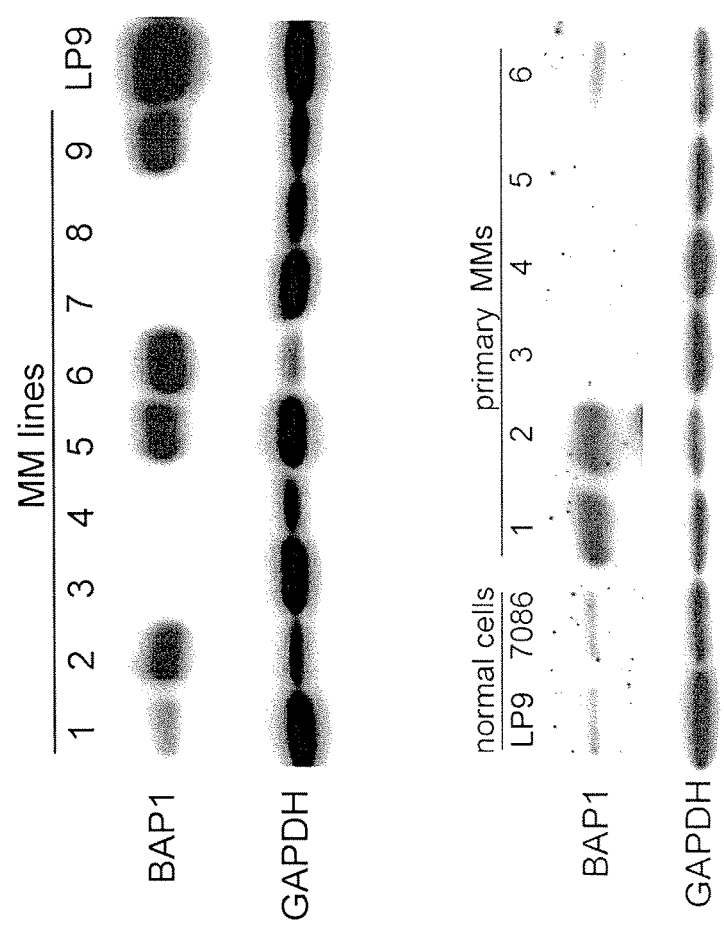
FIG. 6A shows an immunoblot demonstrating frequent loss of detectable BAP1 expression in MM cell lines (top) and sporadic primary tumors (bottom). GAPDH was used as a loading control.
Figure 6B:
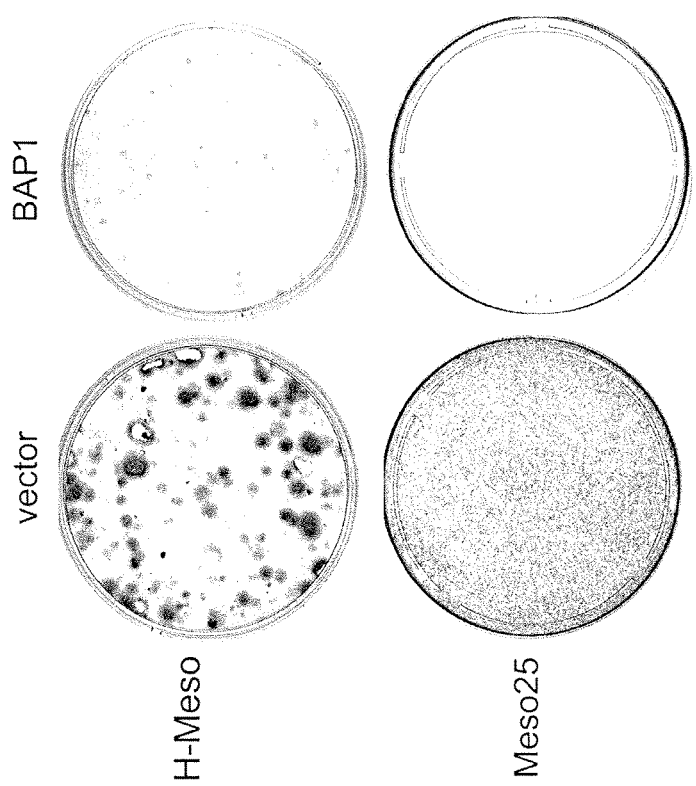
FIG. 6B shows that re-expression of BAP1 in BAP1 deficient MM cells results in decreased colony-forming ability in clonogenic assays. This experiment demonstrates that the presence of wild type BAP1 suppresses tumor cell growth associated with the mutant form of BAP1.

Although tumor protein lysates were not available from these families, frequent loss of BAP1 expression was observed in MM cell lines and sporadic tumors (FIG. 6A). Re-expression of BAP1 in BAP1-deficient MM lines resulted in markedly decreased colony-forming ability in clonogenic assays (FIG. 6B), consistent with BAP1's known role in regulating cell proliferation and viability.

Losses of chromosome 3p21 occur frequently in MM suggesting that loss of one copy of 3p unmasks a mutant recessive allele on the remaining copy. The identification of deletions or other rearrangements of 3p21.1 in tumors from both families for which array-CGH or sequencing data were available is consistent with chromosome 3 alterations uncovering recessive BAP1 mutations.

Frequent somatic mutation of BAP1 was recently reported in metastasizing uveal melanomas, and one case had a germline mutation. The present findings indicate that hereditary alterations in BAP1 predisposes to both uveal melanoma and MM, and possibly to breast, ovarian and renal cell carcinoma, as well as to skin cancer.

In addition, and most importantly, the findings demonstrate the presence of germline BAP1 mutations in members of U.S. families that experience an extremely high incidence of mesothelioma, in spite of very modest exposure to asbestos; thus, the results point to BAP1 as the first reported gene that modulates mineral fiber carcinogenesis. Furthermore, it is shown that BAP1 mutations are associated with a novel hereditary cancer syndrome that predisposes to mesothelioma, uveal melanoma and potentially other cancers. The annual incidence of uveal melanoma is 5 7/10$^6$ in the U.S., similar to mesothelioma. Therefore, it is exceedingly unlikely that the occurrence of both malignancies in the same individual would occur by chance, e.g., if assumed that the two diseases are independent and the joint probability (estimated at 36 per trillion per year) follows a binomial distribution, then the likelihood of three (or more) cases appearing in the U.S. (population ~310 million) per year is $2.3 \times 10^{-7}$.

It is believed that in some individuals uveal melanoma, breast and ovarian cancer may be associated. It is believed that when carriers of BAP1 mutations are exposed to asbestos fibers, MM may predominate over other cancer types.

In family W, the presence of a breast cancer before age 45 and an ovarian cancer is consistent with the hypothesis that the BAP1 mutation is associated with a hereditary form of breast/ovarian cancer, as might be expected given BAP1's relationship with the breast/ovarian cancer susceptibility gene product, BRCA1. BAP1 was identified based on its binding to the RING finger domain of BRCA1 (Jensen D et al. (1998) Oncogene 16:1097-1112). It was found that BAP1 enhances BRCA1-mediated inhibition of breast cancer cell proliferation and proposed that BAP1 acts as a tumor suppressor in the BRCA1 growth control pathway. BAP1 exhibits tumor suppressor activity in cancer cells, and somatic BAP1 mutations have been reported in some breast and lung cancers (Jensen D et al. (1998) Oncogene 16:1097-1112; and, Wood L D et al. (2007) Science 318:1108-13). BAP1 regulates cell proliferation by deubiquitinating host cell factor-1, a cell-cycle regulator critical for BAP1-mediated growth regulation.

Figure 1B:
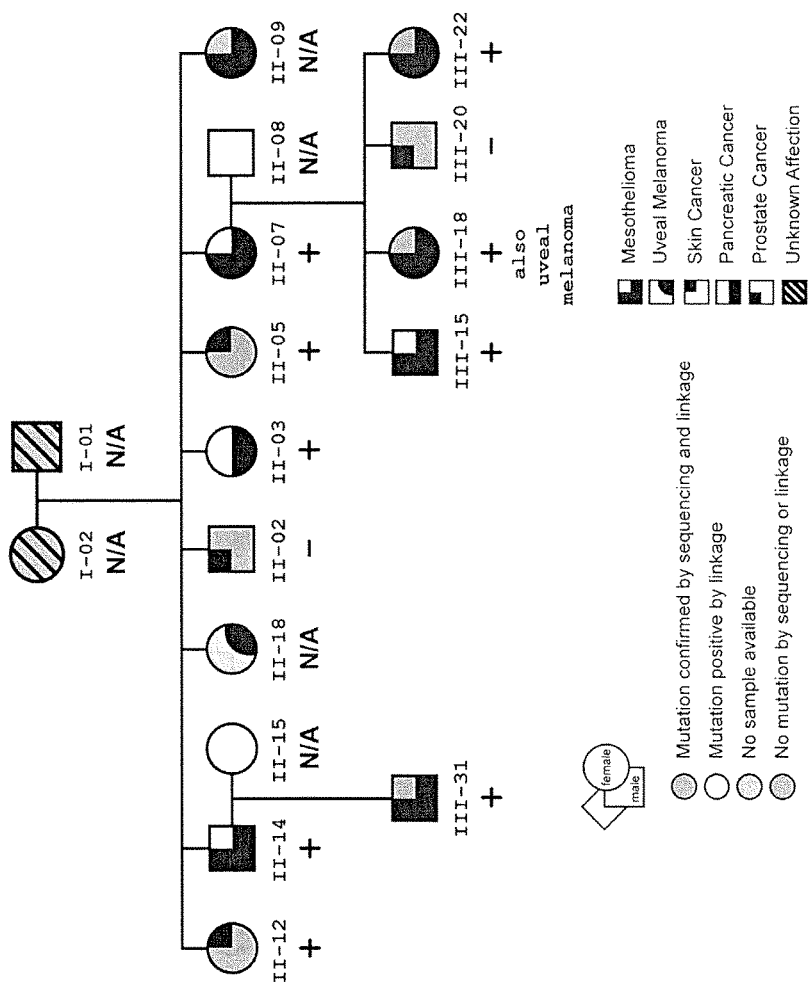
FIG. 1B shows a partial pedigree of family L, having 14 members with cancer, including 7 with MM; showing the presence or absence of germline nonsense mutation. Uveal melanomas were observed in two patients, one of whom (L-III-18) also had MM, while the second had liver cancer. In family W, the presence of a breast cancer before age 45 and an ovarian cancer suggests that the BAP1 mutation is associated with a hereditary form of breast/ovarian cancer, as might be expected given BAP1's relationship with the breast/ovarian cancer susceptibility gene product, BRCA1. In family L, the skin cancers shown were squamous cell carcinomas. Available mesothelioma tumor specimens had germline splice site mutation and either somatic 25-bp deletion (W-III-04T), genomic alteration (W-III-06T), or loss of wild-type BAP1 allele (W-III-08T). A homozygous deletion of BAP1 was seen in mesothelioma specimen L-III-18T.

The identification of germline BAP1 mutations in high-risk MM families indicates that genetic factors play a major role in malignant mesothelioma and susceptibility to carcinogenic mineral fibers and suggest that the BAP1 pathway represents a novel target for preventive and therapeutic intervention in MM. The presence of other tumor types (breast, ovarian, melanoma, pancreatic, renal) in the families reported here, and the existence of germline BAP1 mutations in some uveal melanoma patients (FIG. 1B), suggest the existence of a BAP1-related cancer syndrome, in which MM may predominate possibly when mutation carriers are exposed to carcinogenic fibers. A search of the 1000 Genomes Project database revealed 7 individuals with BAP1 mutations that could alter BAP1 function, providing rationale for mutation screening and appropriate preventive measures in certain high-risk individuals, e.g., asbestos workers and communities along roads paved with gravel containing asbestos or erionite, individuals living in homes containing asbestos, and other environments where individuals may encounter exposure to carcinogenic mineral fibers.

These results provide the first demonstration that genetics influences the risk of mesothelioma, a cancer linked to mineral fiber carcinogenesis. As observed for BRCA1 and BRCA2, which account for only some hereditary breast carcinomas, it appears likely that in addition to BAP1, more genes will be found associated with elevated risk of mesothelioma. Indeed, among the 26 sporadic mesotheliomas studied—and excluding malignancies common in the 6th-8th decades of life, such as skin and prostate carcinomas—nine had been diagnosed with one or more additional tumors (Table 1). Seven of 26 were females, and 2/7 also had uterine leiomyosarcoma, a malignancy with an incidence of ~10/10$^6$ per year in the U.S.; one of them had also uveal melanoma, an unlikely coincidence.

The invention is not limited to the embodiments described and exemplified above, but is capable of variation and modification within the scope of the appended claims.

We claim:

1. A method for delaying the onset of malignant mesothelioma in a human subject experiencing exposure to mineral fibers, wherein the human subject has a germline alteration in the BAP1 gene, comprising:
   obtaining a germline nucleic encoding the BAP1 protein from cells in the subject, and if the nucleic acid comprises an mRNA, optionally converting the mRNA to a cDNA,
   detecting in the nucleic acid the presence of one or more germline alterations that encodes a truncated BAP1 protein biologic activity or no biologic activity, or that results in nonsense—mediated decay of BAP1 protein-encoding mRNA, and that is associated with development of malignant mesothelioma, and
   treating the subject having the one or more germline alterations by reducing the amount of mineral fibers the subject is exposed to
   wherein the germline alterations is a C to T-nonsense mutation in exon 16 at a position corresponding to position 52,436,624; or an A to G mutation at the splice site in intron 6 at a position corresponding to position 52,441,334.

2. The method of claim 1, wherein the germline nucleic acid encoding the BAP1 protein comprises genomic DNA.

3. The method of claim 1, wherein the method comprises obtaining an mRNA encoding the BAP1 protein from cells in the subject, converting the mRNA to a cDNA, and determining whether the cDNA comprises one or more germline alterations that encodes a truncated BAP1 protein having impaired biologic activity or no biologic activity and that is associated with development of malignant mesothelioma in human beings.

4. The method of claim 1, wherein the treatment comprises reducing exposure of the subject to mineral fibers in the environment.

5. The method of claim 4, wherein the mineral fibers comprise asbestos or erionite.

6. The method of claim 1, wherein the determining step comprises sequencing the germline nucleic acid.

7. The method of claim 1, wherein the determining step comprises contacting the germline nucleic acid with a detectably-labeled nucleic acid probe having a sequence that is complementary to one or more germline alterations the encodes a trunctated BAP1protein having impaired biologic activity or no biologic activity and that is associated with the development of malignant mesothelioma in human beings.

8. The method of claim 1, wherein the alteration occurs at or proximal to an exon-intron splice site.

* * * * *

```
                              SEQUENCE LISTING

<160> NUMBER OF SEQ ID NOS: 45

<210> SEQ ID NO 1
<211> LENGTH: 31
<212> TYPE: DNA
<213> ORGANISM: Homo sapiens

<400> SEQUENCE: 1
actctgtttt tccccaggcc cgagccacgc c                                    31

<210> SEQ ID NO 2
<211> LENGTH: 31
<212> TYPE: DNA
<213> ORGANISM: Homo sapiens

<400> SEQUENCE: 2
actctgtttt tccccgggcc cgagccacgc c                                    31

<210> SEQ ID NO 3
<211> LENGTH: 56
<212> TYPE: DNA
<213> ORGANISM: Homo sapiens

<400> SEQUENCE: 3
ggatgatacg tccgtgattg atgatgatat tgtgaataac atgttctttg cccacc         56

<210> SEQ ID NO 4
<211> LENGTH: 25
<212> TYPE: DNA
<213> ORGANISM: Homo sapiens

<400> SEQUENCE: 4
attgatgatg atattgtgaa taaca                                           25

<210> SEQ ID NO 5
<211> LENGTH: 31
<212> TYPE: DNA
<213> ORGANISM: Homo sapiens

<400> SEQUENCE: 5
ggatgatacg tccgtgtgtt ctttgcccac c                                    31

<210> SEQ ID NO 6
<211> LENGTH: 30
<212> TYPE: DNA
<213> ORGANISM: Homo sapiens

<400> SEQUENCE: 6
taatagccat gccaggcccg agccacgcca                                      30

<210> SEQ ID NO 7
<211> LENGTH: 32
<212> TYPE: DNA
<213> ORGANISM: Homo sapiens

<400> SEQUENCE: 7
ctaccccatt gaccatgggc cctgggggga gg                                   32

<210> SEQ ID NO 8
```

```
<211> LENGTH: 30
<212> TYPE: DNA
<213> ORGANISM: Homo sapiens

<400> SEQUENCE: 8
taatagccat gccagggccc tgggggagg                                          30

<210> SEQ ID NO 9
<211> LENGTH: 31
<212> TYPE: DNA
<213> ORGANISM: Homo sapiens

<400> SEQUENCE: 9
atctccatgc tggctcagga aggtgagggg a                                       31

<210> SEQ ID NO 10
<211> LENGTH: 31
<212> TYPE: DNA
<213> ORGANISM: Homo sapiens

<400> SEQUENCE: 10
atctccatgc tggcttagga aggtgagggg a                                       31

<210> SEQ ID NO 11
<211> LENGTH: 37
<212> TYPE: DNA
<213> ORGANISM: Homo sapiens

<400> SEQUENCE: 11
accttcagag caaatgtcag gggtgagtgg ctgtaca                                 37

<210> SEQ ID NO 12
<211> LENGTH: 32
<212> TYPE: DNA
<213> ORGANISM: Homo sapiens

<400> SEQUENCE: 12
accttcagag caaatgagtg agtggctgta ca                                      32

<210> SEQ ID NO 13
<211> LENGTH: 6
<212> TYPE: DNA
<213> ORGANISM: Homo sapiens

<400> SEQUENCE: 13 tcaggg                                                                    6

<210> SEQ ID NO 14
<211> LENGTH: 29
<212> TYPE: DNA
<213> ORGANISM: Homo sapiens

<400> SEQUENCE: 14
gctcaggaag gtgagggat gcgctgctg                                           29

<210> SEQ ID NO 15
<211> LENGTH: 28
<212> TYPE: DNA
<213> ORGANISM: Homo sapiens

<400> SEQUENCE: 15
ggggtgctga gtccctggc gctgacag                                            28
```

```
<210> SEQ ID NO 16
<211> LENGTH: 27
<212> TYPE: DNA
<213> ORGANISM: Homo sapiens

<400> SEQUENCE: 16
ggggtgctga gtccctggcg ctgacag                                          27

<210> SEQ ID NO 17
<211> LENGTH: 31
<212> TYPE: DNA
<213> ORGANISM: Homo sapiens

<400> SEQUENCE: 17
gcccttgagt ggggagaaat actcacccaa g                                     31

<210> SEQ ID NO 18
<211> LENGTH: 27
<212> TYPE: DNA
<213> ORGANISM: Homo sapiens

<400> SEQUENCE: 18
gcccttgagt ggggagaaat acccaag                                          27

<210> SEQ ID NO 19
<211> LENGTH: 43
<212> TYPE: DNA
<213> ORGANISM: Homo sapiens

<400> SEQUENCE: 19
gcccttgagt ggggagaaat actcacccaa ggagctgctg gca                        43

<210> SEQ ID NO 20
<211> LENGTH: 39
<212> TYPE: DNA
<213> ORGANISM: Homo sapiens

<400> SEQUENCE: 20
gcccttgagt ggggagaaat acccaaggag ctgctggca                             39

<210> SEQ ID NO 21
<211> LENGTH: 31
<212> TYPE: DNA
<213> ORGANISM: Homo sapiens

<400> SEQUENCE: 21
ggcgtggctc gggcctgggg aaaaacagag t                                     31

<210> SEQ ID NO 22
<211> LENGTH: 31
<212> TYPE: DNA
<213> ORGANISM: Homo sapiens

<400> SEQUENCE: 22
ggcgtggctc gggcccgggg aaaaacagag t                                     31

<210> SEQ ID NO 23
<211> LENGTH: 56
<212> TYPE: DNA
<213> ORGANISM: Homo sapiens

<400> SEQUENCE: 23
ggtgggcaaa gaacatgtta ttcacaatat catcatcaat cacggacgta tcatcc          56
```

<210> SEQ ID NO 24
<211> LENGTH: 25
<212> TYPE: DNA
<213> ORGANISM: Homo sapiens

<400> SEQUENCE: 24
tgttattcac aatatcatca tcaat                                          25

<210> SEQ ID NO 25
<211> LENGTH: 31
<212> TYPE: DNA
<213> ORGANISM: Homo sapiens

<400> SEQUENCE: 25
ggtgggcaaa gaacacacgg acgtatcatc c                                   31

<210> SEQ ID NO 26
<211> LENGTH: 30
<212> TYPE: DNA
<213> ORGANISM: Homo sapiens

<400> SEQUENCE: 26
tggcgtggct cgggcctggc atggctatta                                     30

<210> SEQ ID NO 27
<211> LENGTH: 32
<212> TYPE: DNA
<213> ORGANISM: Homo sapiens

<400> SEQUENCE: 27 cctccccca gggcccatgg tcaatggggt ag                                   32

<210> SEQ ID NO 28
<211> LENGTH: 30
<212> TYPE: DNA
<213> ORGANISM: Homo sapiens

<400> SEQUENCE: 28 cctccccca gggccctggc atggctatta                                      30

<210> SEQ ID NO 29
<211> LENGTH: 31
<212> TYPE: DNA
<213> ORGANISM: Homo sapiens

<400> SEQUENCE: 29
tcccctcacc ttcctgagcc agcatggaga t                                   31

<210> SEQ ID NO 30
<211> LENGTH: 31
<212> TYPE: DNA
<213> ORGANISM: Homo sapiens

<400> SEQUENCE: 30
tcccctcacc ttcctaagcc agcatggaga t                                   31

<210> SEQ ID NO 31
<211> LENGTH: 37
<212> TYPE: DNA
<213> ORGANISM: Homo sapiens

<400> SEQUENCE: 31
tgtacagcca ctcacccctg acatttgctc tgaaggt                             37

<210> SEQ ID NO 32
<211> LENGTH: 32
<212> TYPE: DNA
<213> ORGANISM: Homo sapiens

<400> SEQUENCE: 32
tgtacagcca ctcactcatt tgctctgaag gt                          32

<210> SEQ ID NO 33
<211> LENGTH: 5
<212> TYPE: DNA
<213> ORGANISM: Homo sapiens

<400> SEQUENCE: 33 cctga                                                        5

<210> SEQ ID NO 34
<211> LENGTH: 29
<212> TYPE: DNA
<213> ORGANISM: Homo sapiens

<400> SEQUENCE: 34
cagcagcgca tcccctcacc ttcctgagc                              29

<210> SEQ ID NO 35
<211> LENGTH: 28
<212> TYPE: DNA
<213> ORGANISM: Homo sapiens

<400> SEQUENCE: 35
ctgtcagcgc cagggactc agcacccc                                28

<210> SEQ ID NO 36
<211> LENGTH: 27
<212> TYPE: DNA
<213> ORGANISM: Homo sapiens

<400> SEQUENCE: 36
ctgtcagcgc cagggactca gcacccc                                27

<210> SEQ ID NO 37
<211> LENGTH: 31
<212> TYPE: DNA
<213> ORGANISM: Homo sapiens

<400> SEQUENCE: 37
cttgggtgag tatttctccc cactcaaggg c                           31

<210> SEQ ID NO 38
<211> LENGTH: 27
<212> TYPE: DNA
<213> ORGANISM: Homo sapiens

<400> SEQUENCE: 38
cttgggtatt tctccccact caagggc                                27

<210> SEQ ID NO 39
<211> LENGTH: 43
<212> TYPE: DNA
<213> ORGANISM: Homo sapiens

<400> SEQUENCE: 39

```
tgccagcagc tccttgggtg agtatttctc cccactcaag ggc          43
```

<210> SEQ ID NO 40
<211> LENGTH: 39
<212> TYPE: DNA
<213> ORGANISM: Homo sapiens

<400> SEQUENCE: 40

```
tgccagcagc tccttgggta tttctcccca ctcaagggc               39
```

<210> SEQ ID NO 41
<211> LENGTH: 3599
<212> TYPE: DNA
<213> ORGANISM: Homo sapiens

<400> SEQUENCE: 41

```
gcccgttgtc tgtgtgtggg actgagggc cccggggcg gtggggctc ccggtgggg     60
cagcggtggg gagggagggc ctggacatgg cgctgagggg ccgccccgcg ggaagatgaa  120
taagggctgg ctggagctgg agagcgaccc aggcctcttc accctgctcg tggaagattt  180
cggtgtcaag ggggtgcaag tggaggagat ctacgacctt cagagcaaat gtcagggccc  240
tgtatatgga tttatcttcc tgttcaaatg gatcgaagag cgccggtccc ggcgaaaggt  300
ctctaccttg gtggatgata cgtccgtgat tgatgatgat attgtgaata acatgttctt  360
tgcccaccag ctgataccca actcttgtgc aactcatgcc ttgctgagcg tgctcctgaa  420
ctgcagcagc gtggacctgg acccacccct gagtcgcatg aaggacttca ccaagggttt  480
cagccctgag agcaaaggat atgcgattgg caatgccccg gagttggcca aggcccataa  540
tagccatgcc aggcccgagc acgccacct ccctgagaag cagaatggcc ttagtgcagt  600
gcggaccatg gaggcgttcc actttgtcag ctatgtgcct atcacaggcc ggctctttga  660
gctggatggg ctgaaggtct accccattga ccatgggccc tgggggagg acgaggagtg  720
gcagacaaag gccggcgggg tcatcatgga gcgtatcggc ctcgccactg caggggagcc  780
ctaccacgac atccgcttca acctgatggc agtggtgccc gaccgcagga tcaagtatga  840
ggccaggctg catgtgctga aggtgaaccg tcagacagta ctagaggctc tgcagcagct  900
gataagagta acacagccag agctgattca gacccacaag tctcaagagt cacagctgcc  960
tgaggagtcc aagtcagcca gcaacaagtc ccgctggtg ctggaagcaa cagggcccc   1020
tgcagcctct gagggcaacc acacagatgg tgcagaggag gcggctggtt catgcgcaca  1080
agccccatcc cacagccctc ccaacaaacc caagctagtg gtgaagcctc caggcagcag  1140
cctcaatggg gttcacccca accccactcc cattgtccag cggctgccgg cctttctaga  1200
caatcacaat tatgccaagt cccccatgca ggaggaagaa gacctggcgg caggtgtggg  1260
ccgcagccga gttccagtcc gcccacccca gcagtactca gatgatgagg atgactatga  1320
ggatgacgag gaggatgacg tgcagaacac caactctgcc cttaggtata agggggaaggg  1380
aacagggaag ccaggggcat tgagcggttc tgctgatggg caactgtcag tgctgcagcc  1440
caacaccatc aacgtcttgg ctgagaagct caaagagtcc cagaaggacc tctcaattcc  1500
tctgtccatc aagactagca gcggggctgg gagtccggct gtggcagtgc ccacacactc  1560
gcagccctca cccaccccca gcaatgagag tacagacacg gcctctgaga tcggcagtgc  1620
tttcaactcg ccactgcgct cgcctatccg ctcagccaac ccgacgcggg cctccagccc  1680
tgtcacctcc cacatctcca aggtgctttt tggagaggat gacagcctgc tgcgtgttga  1740
ctgcatacgc tacaaccgtg ctgtccgtga tctgggtcct gtcatcagca caggcctgct  1800
```

```
gcacctggct gaggatgggg tgctgagtcc cctggcgctg acagagggtg ggaagggttc   1860
ctcgccctcc atcagaccaa tccaaggcag ccaggggtcc agcagcccag tggagaagga   1920
ggtcgtggaa gccacggaca gcagagagaa gacggggatg gtgaggcctg gcgagccctt   1980
gagtggggag aaatactcac ccaaggagct gctggcactg ctgaagtgtg tggaggctga   2040
gattgcaaac tatgaggcgt gcctcaagga ggaggtagag aagaggaaga agttcaagat   2100
tgatgaccag agaaggaccc acaactacga tgagttcatc tgcaccttta tctccatgct   2160
ggctcaggaa ggcatgctgg ccaacctagt ggagcagaac atctccgtgc ggcggcgcca   2220
aggggtcagc atcggccggc tccacaagca gcggaagcct gaccggcgga aacgctctcg   2280
cccctacaag gccaagcgcc agtgaggact gctggccctg actctgcagc ccactcttgc   2340
cgtgtggccc tcaccagggt ccttccctgc cccacttccc cttttcccag tattactgaa   2400
tagtcccagc tggagagtcc aggccctggg aatgggagga accaggccac attccttcca   2460
tcgtgccctg aggcctgaca cggcagatca gccccatagt gctcaggagg cagcatctgg   2520
agttggggca cagcgaggta ctgcagcttc ctccacagcc ggctgtggag cagcaggacc   2580
tggcccttct gcctgggcag cagaatatat attttaccta tcagagacat ctattttct   2640 gggctccaac ccaacatgcc accatgttga cataagttcc tacctgacta tgctttctct   2700
cctaggagct gtcctggtgg gcccaggtcc ttgtatcatg ccacggtccc aactacaggg   2760
tcctagctgg gggcctgggt gggccctggg ctctgggccc tgctgctcta gccccagcca   2820
ccagcctgtc cctgttgtaa ggaagccagg tcttctctct tcattcctct taggagagtg   2880
ccaaactcag ggacccagca ctgggctggg ttgggagtag ggtgtcccag tggggttggg   2940
gtgagcaggc tgctgggatc ccatggcctg agcagagcat gtgggaactg ttcagtggcc   3000
tgtgaactgt cttccttgtt ctagccaggc tgttcaagac tgctctccat agcaaggttc   3060
tagggctctt cgccttcagt gttgtggccc tagctatggg cctaaattgg gctctaggtc   3120
tctgtccctg gcgcttgagg ctcagaagag cctctgtcca gcccctcagt attaccatgt   3180
ctccctctca ggggtagcag agacagggtt gcttatagga agctggcacc actcagctct   3240
tcctgctact ccagtttcct cagcctctgc aaggcactca gggtggggga cagcaggatc   3300
aagacaaccc gttggagccc ctgtgttcca gaggacctga tgccaagggg taatgggccc   3360
agcagtgcct ctggagccca ggccccaaca cagccccatg gcctctgcca gatggctttg   3420
aaaaaggtga tccaagcagg ccccttatc tgtacatagt gactgagtgg ggggtgctgg   3480
caagtgtggc agctgcctct gggctgagca cagcttgacc cctctagccc ctgtaaatac   3540
tggatcaatg aatgaataaa actctcctaa gaatctcctg agaaaaaaaa aaaaaaaa   3599
```

<210> SEQ ID NO 42
<211> LENGTH: 3600
<212> TYPE: DNA
<213> ORGANISM: Homo sapiens

<400> SEQUENCE: 42

```
gcccgttgtc tgtgtgtggg actgaggggc ccgggggggcg gtgggggctc ccggtggggg     60
cagcggtggg gagggagggc ctggacatgg cgctgagggg ccgccccgcg ggaagatgaa    120
taagggctgg ctggagctgg agagcgaccc aggcctcttc accctgctcg tggaagattt    180
cggtgtcaag ggggtgcaag tggagggagat ctacgacctt cagagcaaat gtcagggccc    240
tgtatatgga tttatcttcc tgttcaaatg gatcgaagag cgccggtccc ggcgaaaggt    300
```

```
ctctaccttg gtggatgata cgtccgtgat tgatgatgat attgtgaata acatgttctt    360
tgcccaccag ctgataccca actcttgtgc aactcatgcc ttgctgagcg tgctcctgaa    420
ctgcagcagc gtggacctgg gacccaccct gagtcgcatg aaggacttca ccaagggttt    480
cagccctgag agcaaaggat atgcgattgg caatgccccg gagttggcca aggcccataa    540
tagccatgcc aggcccgagc cacgccacct ccctgagaag cagaatggcc ttagtgcagt    600
gcggaccatg gaggcgttcc actttgtcag ctatgtgcct atcacaggcc ggctctttga    660
gctggatggg ctgaaggtct accccattga ccatgggccc tgggggagg acgaggagtg     720
gacagacaag gcccggcggg tcatcatgga gcgtatcggc ctcgccactg caggggagcc    780
ctaccacgac atccgcttca acctgatggc agtggtgccc gaccgcagga tcaagtatga    840
ggccaggctg catgtgctga aggtgaaccg tcagacagta ctagaggctc tgcagcagct    900
gataagagta acacagccag agctgattca gacccacaag tctcaagagt cacagctgcc    960
tgaggagtcc aagtcagcca gcaacaagtc cccgctggtg ctggaagcaa acagggcccc   1020
tgcagcctct gagggcaacc acacagatgg tgcagaggag gcggctggtt catgcgcaca   1080
agccccatcc cacagccctc caacaaacc caagctagtg gtgaagcctc caggcagcag    1140
cctcaatggg gttcacccca accccactcc cattgtccag cggctgccgg ccttttctaga   1200
caatcacaat tatgccaagt cccccatgca ggaggaagaa gacctggcgg caggtgtggg   1260
ccgcagccga gttccagtcc gcccacccca gcagtactca gatgatgagg atgactatag   1320
aggatgacga ggaggatgac gtgcagaaca ccaactctgc ccttaggtat aaggggaagg   1380
gaacagggaa gccaggggca ttgagcggtt ctgctgatgg gcaactgtca gtgctgcagc   1440
ccaacaccat caacgtcttg gctgagaagc tcaaagagtc ccagaaggac ctctcaattc   1500
ctctgtccat caagactagc agcggggctg ggagtccggc tgtggcagtg cccacacact   1560
cgcagccctc acccaccccc agcaatgaga gtacagacac ggcctctgag atcggcagtg   1620
ctttcaactc gccactgcgc tcgcctatcc gctcagccaa cccgacgcgg ccctccagcc   1680
ctgtcacctc ccacatctcc aaggtgcttt ttggagagga tgacagcctg ctgcgtgttg   1740
actgcatacg ctacaaccgt gctgtccgtg atctgggtcc tgtcatcagc acaggcctgc   1800
tgcacctggc tgaggatggg gtgctgagtc ccctggcgct gacagagggt gggaagggtt   1860
cctcgccctc catcagacca atccaaggca gccaggggtc cagcagccca gtggagaagg   1920
aggtcgtgga agccacggac agcagagaga agacggggat ggtgaggcct ggcgagccct   1980
tgagtgggga gaaatactca cccaaggagc tgctggcact gctgaagtgt gtggaggctg   2040
agattgcaaa ctatgaggcg tgcctcaagg aggaggtaga agagagggaag aagttcaaga   2100
ttgatgacca gagaaggacc cacaactacg atgagttcat ctgcaccttt atctccatgc   2160
tggctcagga aggcatgctg gccaacctag tggagcagaa catctccgtg cggcggcgcc   2220
aaggggtcag catcggccgg ctccacaagc agcggaagcc tgaccggcgg aaacgctctc   2280
gcccctacaa ggccaagcgc cagtgaggac tgctggccct gactctgcag cccactcttg   2340
ccgtgtggcc ctcaccaggg tccttccctg ccccacttcc ccttttccca gtattactga   2400
atagtcccag ctgagagtc caggccctgg gaatgggagg aaccaggcca cattccttcc   2460
atcgtgccct gaggcctgac acggcagatc agccccatag tgctcaggag cagcatctg    2520
gagttggggc acagcgaggt actgcagctt cctccacagc cggctgtgga gcagcaggac   2580
ctggcccttc tgcctgggca gcagaatata tattttacct atcagagaca tctatttttc   2640
tgggctccaa cccaacatgc caccatgttg acataagttc ctacctgact atgctttctc   2700
```

```
tcctaggagc tgtcctggtg ggcccaggtc cttgtatcat gccacggtcc caactacagg    2760
gtcctagctg ggggcctggg tgggccctgg gctctgggcc ctgctgctct agccccagcc    2820
accagcctgt ccctgttgta aggaagccag gtcttctctc ttcattcctc ttaggagagt    2880
gccaaactca gggacccagc actgggctgg gttgggagta gggtgtccca gtggggttgg    2940
ggtgagcagg ctgctgggat cccatggcct gagcagagca tgtgggaact gttcagtggc    3000
ctgtgaactg tcttccttgt tctagccagg ctgttcaaga ctgctctcca tagcaaggtt    3060
ctagggctct tcgccttcag tgttgtggcc ctagctatgg gcctaaattg ggctctaggt    3120
ctctgtccct ggcgcttgag gctcagaaga gcctctgtcc agcccctcag tattaccatg    3180
tctccctctc aggggtagca gagacagggt tgcttatagg aagctggcac cactcagctc    3240
ttcctgctac tccagtttcc tcagcctctg caaggcactc agggtggggg acagcaggat    3300
caagacaacc cgttggagcc cctgtgttcc agaggacctg atgccaaggg gtaatgggcc    3360
cagcagtgcc tctggagccc aggccccaac acagcccat ggcctctgcc agatggcttt    3420
gaaaaaggtg atccaagcag gccccttat ctgtacatag tgactgagtg gggggtgctg    3480
gcaagtgtgg cagctgcctc tgggctgagc acagcttgac ccctctagcc cctgtaaata    3540
ctggatcaat gaatgaataa aactctccta agaatctcct gagaaaaaaa aaaaaaaaaa    3600

<210> SEQ ID NO 43
<211> LENGTH: 10
<212> TYPE: PRT
<213> ORGANISM: Homo sapiens

<400> SEQUENCE: 43

Ile Ser Met Leu Ala Gln Glu Gly Glu Gly
1               5                   10

<210> SEQ ID NO 44
<211> LENGTH: 7
<212> TYPE: PRT
<213> ORGANISM: Homo sapiens

<400> SEQUENCE: 44

Leu Gln Ser Lys Cys Gln Gly
1               5

<210> SEQ ID NO 45
<211> LENGTH: 4
<212> TYPE: PRT
<213> ORGANISM: Homo sapiens

<400> SEQUENCE: 45

Leu Gln Ser Lys
1
```